US012611497B2

(12) United States Patent
Suffritti et al.

(10) Patent No.: US 12,611,497 B2
(45) Date of Patent: Apr. 28, 2026

(54) PERITONEAL DIALYSIS CIRCUIT

(71) Applicants: Vantive Health GmbH, Glattpark
(CH); Vantive US Healthcare LLC,
Deerfield, IL (US)

(72) Inventors: Mauro Suffritti, Modena (IT); **Mauro
Gusella**, Modena (IT)

(73) Assignees: Vantive US Healthcare LLC,
Deerfield, IL (US); **Vantive Health
GmbH**, Glattpark (CH)

( * ) Notice: Subject to any disclaimer, the term of this
patent is extended or adjusted under 35
U.S.C. 154(b) by 288 days.

(21) Appl. No.: 18/210,228

(22) Filed: Jun. 15, 2023

(65) Prior Publication Data

US 2023/0405199 A1     Dec. 21, 2023

(30) Foreign Application Priority Data

Jun. 17, 2022    (EP) .................................... 22179556

(51) Int. Cl.
*A61M 1/28*        (2006.01)
*A61M 1/14*        (2006.01)
*A61M 1/16*        (2006.01)

(52) U.S. Cl.
CPC ............ *A61M 1/282* (2014.02); *A61M 1/155*
(2022.05); *A61M 1/1656* (2013.01); *A61M
1/1658* (2013.01); *A61M 1/166* (2014.02);
*A61M 1/1668* (2014.02); *A61M 1/287*
(2013.01); *A61M 1/565* (2022.05);
(Continued)

(58) Field of Classification Search
CPC .. A61M 1/155; A61M 1/1565; A61M 1/1656;
A61M 1/1658; A61M 1/166; A61M
1/1668; A61M 1/282; A61M 1/287;
A61M 2205/3334; A61M 2205/3368;
A61M 2205/36
See application file for complete search history.

(56) References Cited

U.S. PATENT DOCUMENTS

| | | |
|---|---|---|
| 4,190,047 A | 2/1980 | Jacobsen et al. |
| 5,944,684 A | 8/1999 | Roberts et al. |
| 6,846,299 B2 | 1/2005 | Masuda et al. |

(Continued)

FOREIGN PATENT DOCUMENTS

| | | |
|---|---|---|
| DE | 19540079 A1 | 4/1997 |
| EP | 2029192 B1 | 12/2014 |

(Continued)

*Primary Examiner* — John Kim
(74) *Attorney, Agent, or Firm* — K&L Gates LLP

(57) ABSTRACT

A peritoneal dialysis fluid circuit comprising a patient line,
a delivery line configured to supply fresh dialysis fluid
towards the patient line, a withdrawal line configured to
withdraw spent dialysis fluid from the patient line, a first
pump arranged on the delivery line and configured to supply
fresh dialysis fluid towards the patient line, and a second
pump arranged on the withdrawal line and configured to
withdraw spent dialysis fluid from the patient line. The fluid
circuit further comprises a control unit configured to per-
form a peritoneal dialysis procedure. The peritoneal dialysis
procedure comprises commanding activation of the first
pump at a first flow rate, and activation of the second pump
at a second flow rate different from the first flow rate: the
first pump and the second pump are active simultaneously to
provide the first flow rate and the second flow rate.

19 Claims, 7 Drawing Sheets

(52) U.S. Cl.
CPC ............... *A61M 2205/3334* (2013.01); *A61M 2205/3368* (2013.01); *A61M 2205/36* (2013.01)

(56) References Cited

U.S. PATENT DOCUMENTS

| | | |
|---|---|---|
| 8,096,969 B2 | 1/2012 | Roberts et al. |
| 2004/0019312 A1 | 1/2004 | Childers et al. |
| 2010/0004588 A1 | 1/2010 | Yeh et al. |
| 2011/0184339 A1 | 7/2011 | Tan |
| 2013/0184638 A1 | 7/2013 | Scarpaci et al. |
| 2020/0061273 A1 | 2/2020 | Hogard et al. |

FOREIGN PATENT DOCUMENTS

| | | | |
|---|---|---|---|
| EP | 1991289 B1 | | 6/2015 |
| WO | 2007143497 A2 | | 12/2007 |
| WO | 2015007596 A1 | | 1/2015 |
| WO | WO 2019/16908 A | * | 9/2019 |

* cited by examiner

PERITONEAL DIALYSIS CIRCUIT

PRIORITY CLAIM

This application claims priority to European Patent Application No. 22179556.0, filed Jun. 17, 2022, the entire disclosure of which is incorporated herein by reference.

FIELD OF THE INVENTION

The present disclosure relates generally to peritoneal dialysis circuit.

In particular the present disclosure further relates to a peritoneal dialysis apparatus comprising the circuit, and a process for performing a peritoneal dialysis treatment.

BACKGROUND

Due to various causes, a person's renal system may fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly.

Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal cavity via a catheter. The dialysis fluid is in contact with the peritoneal membrane in the patient's peritoneal cavity. Waste, toxins, and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins, and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis, and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal cavity, wherein the transfer of waste, toxins, and excess water takes place. After a dwell period, the patient repeats the manual dialysis procedure, for example, four times per day. Manual peritoneal dialysis requires a significant amount of time and effort from the patient, leaving ample room for improvement.

APD is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the chamber and for the transfer of waste, toxins, and excess water to take place. The source may include multiple liters of dialysis fluid including several solution bags.

APD machines pump used or spent dialysate from the patient's peritoneal cavity, though the catheter, to drain. As with the manual process, several drain, fill and dwell cycles occur during dialysis. A "last fill" may occur at the end of the APD treatment. The last fill fluid may remain in the peritoneal cavity of the patient until the start of the next treatment, or may be manually emptied at some point during the day.

In any of the above modalities using an automated machine, the automated machine operates typically with a disposable set, which is discarded after a single use.

Circuits for peritoneal dialysis may comprise one or two pumps to supply fresh dialysis fluid into the patient's abdomen and to withdraw exhausted dialysate fluid after a dwell time. The amount of fluid supplied to the patient, as well as the supply rate of the fluid, must be controlled and set within preset thresholds, in order to ensure that the treatment is carried out according to the predefined provisions. Notably, the accuracy in determining the actual amount of fluid supplied to and withdrawn from the patient is of primary importance during the peritoneal dialysis treatment. The flow rate during supplying and/or during withdrawing of the fluid should be very low, to avoid pain and/or health risks for the patient: for example the flow rate may be around 5 ml/min. Unfortunately, the lower is the flow rate, the lower is the accuracy of the sensors directed to measure the flow rate and the amount of fluid supplied to and withdrawn from the patient's abdomen. In order to measure small values of flow rates, the peritoneal dialysis apparatus should either use very expensive sensors to ensure the proper accuracy or accept measuring errors using more economic sensors.

However, especially for APD and CAPD apparatuses, the costs should be kept as lower as possible, while still ensuring the proper accuracy in fluid measurement.

Other apparatus for peritoneal dialysis are known from document WO2007/143497 and from document US2011/184339.

OBJECTIVES

The objective of this invention is therefore to at least partially solve one or more of the drawbacks and/or limitations of the previous solutions.

A first objective of one or more of the described embodiments is to provide a peritoneal dialysis apparatus able to improve measurement accuracy of the flow rate.

A further objective of one or more of the described embodiments is to provide a peritoneal dialysis apparatus able to ensure accuracy in flow rate measurement, whilst keeping manufacturing costs low.

A further aim of one or more of the described embodiments is to provide a peritoneal dialysis apparatus able to ensure accuracy in flow rate measurement over a wide range of flow rates directed to supply fluid to, or withdraw fluid from, the patient.

A further aim of one or more of the described embodiments is to provide a peritoneal dialysis apparatus able to use standard and commercial volumetric fluid pumps without impacting on the flow rate delivery accuracy.

A further goal of one or more of the described embodiments is to provide a peritoneal dialysis apparatus that is reliable in guaranteeing the accuracy of flow measurement, using low-cost commercial components operating at their optimal operating points.

A further objective is to provide a peritoneal dialysis apparatus able to ensure accuracy in flow rate delivery and measurement, whilst avoiding massive changes to the design of the known apparatuses, in order to minimize redesigning costs.

SUMMARY

A 1st aspect is directed to a peritoneal dialysis fluid circuit (10) comprising:

at least one patient line extending between a first end, configured to connect to the patient's abdomen, and a second end;

a delivery line connected to the second end of the at least one patient line and configured to supply fresh dialysis fluid towards the at least one patient line;

a withdrawal line connected to the second end of the at least one patient line and configured to withdraw spent dialysis fluid from the at least one patient line;

a first pump arranged on the delivery line, and configured to supply fresh dialysis fluid towards the patient line;

a second pump arranged on the withdrawal line, and configured to withdraw spent dialysis fluid from the patient line;

a control unit operatively connected to the first pump and to the second pump, said control unit being configured to perform a peritoneal dialysis procedure comprising the step of:

commanding activation of the first pump at a first flow rate, and commanding activation of the second pump at a second flow rate different from the first flow rate, and wherein the first pump and the second pump are active simultaneously to deliver the first flow rate and the second flow rate. A 2nd aspect is directed to a process for performing a peritoneal dialysis treatment through a peritoneal dialysis fluid circuit (10) comprising:

at least one patient line extending between a first end, configured to connect to the patient's abdomen, and a second end;

a delivery line connected to the second end of the at least one patient line and configured to supply fresh dialysis fluid towards the at least one patient line;

a withdrawal line connected to the second end of the at least one patient line and configured to withdraw spent dialysis fluid from the at least one patient line;

a first pump arranged on the delivery line, and configured to supply fresh dialysis fluid towards the patient line;

a second pump arranged on the withdrawal line, and configured to withdraw spent dialysis fluid from the patient line;

a control unit operatively connected to the first pump and to the second pump, said process comprising performing a peritoneal dialysis procedure (by said control unit) comprising the step of:

commanding activation of the first pump at a first flow rate, and commanding activation of the second pump at a second flow rate different from the first flow rate, and wherein the first pump and the second pump are active simultaneously to deliver the first flow rate and the second flow rate.

A further aspect is directed to a peritoneal dialysis apparatus (20) comprising a housing (22), said housing (22) carrying a fluid circuit (10) comprising:

at least one patient line extending between a first end, configured to connect to the patient's abdomen, and a second end;

a delivery line connected to the second end of the at least one patient line and configured to supply fresh dialysis fluid towards the at least one patient line;

a withdrawal line connected to the second end of the at least one patient line and configured to withdraw spent dialysis fluid from the at least one patient line;

a first pump arranged on the delivery line, and configured to supply fresh dialysis fluid towards the patient line;

a second pump arranged on the withdrawal line, and configured to withdraw spent dialysis fluid from the patient line;

a control unit operatively connected to the first pump and to the second pump, said control unit being configured to perform a peritoneal dialysis procedure comprising the step of.

commanding activation of the first pump at a first flow rate, and commanding activation of the second pump at a second flow rate different from the first flow rate, and wherein the first pump and the second pump are active simultaneously to deliver the first flow rate and the second flow rate.

In particular, a fluid recirculation loop is defined inside the PD fluid circuit (10) and includes the delivery line (11) and the withdrawal line (12). In more detail, the fluid recirculation loop is a closed loop and optionally further comprises a recirculation portion (13) extending from an outlet of the second pump (70*b*) up to an inlet of the first pump (70*a*) according a fluid direction (A) defined by the first pump (70*a*) and the second pump (70*b*); according to embodiments of the present disclosure, the recirculation portion (13) does not include the second end (28*b*) of the patient line (28).

The first end (28*a*) of the patient line (28) removably connects either to disposable patient line connected to the patient implanted catheter, or directly to the patient implanted catheter.

The patient line (28) is generally non disposable (being disinfected after the treatment end) or at least partly not disposable; the disposable part being discarded after treatment and the non-disposable part that includes the second end (28*b*) is disinfected after the treatment.

The recirculation loop is a closed loop allowing fluid recirculation. The PD fluid circuit (10) may of course comprise fluid lines entering and/or exiting into the recirculation loop. Said fluid lines may be closed by respective valves or not (i.e., valve present, but closed or valve absent).

Regardless the presence of open/closed fluid lines, the recirculation loop may allow fluid flow to recirculate within itself.

In a 3rd aspect according to any one of the preceding aspects, a difference between the first flow rate and the second flow rate defines an exchange parameter value representing the exchange flow rate of dialysis fluid with the patient in the patient line (28).

In a 4th aspect according to any one of the preceding aspects, the peritoneal dialysis procedure comprises the step of calculating said exchange parameter value based on the difference between the first flow rate and the second flow rate.

In a 5th aspect according to any one of the preceding aspects, the peritoneal dialysis procedure comprises the step of receiving as input a desired exchange parameter value representing the exchange flow rate of dialysis fluid with the patient in the patient line (28).

In a 6th aspect according to the preceding aspect, the peritoneal dialysis procedure comprises the step of setting a difference between the first flow rate and the second flow rate based on said desired exchange parameter value, in particular to obtain said desired exchange flow rate of dialysis fluid in the patient line (28).

In a 7th aspect according to any one of the preceding aspects, the peritoneal dialysis procedure (200) comprises a step of determining or receiving an optimal first flow rate and/or an optimal second flow rate, said optimal first flow rate and/or said optimal second flow rate representing in particular an optimal operating condition for the first pump (70*a*) and for the second pump (70*b*).

In other terms, since the dialysis fluid flow rate (for either filling fresh fluid or withdrawing spent fluid) that is generated in the patient line (28) is defined by the difference in flow rate between the first pump (70*a*) and the second pump (70*b*), both pumps may be driven substantially at their working set point keeping high efficiency, high reliability and minimizing the noise.

In an 8th aspect according to the preceding aspect, the peritoneal dialysis procedure (200) comprises a step of setting the first flow rate of the first pump (70*a*) within a first range of +30% of the optimal first flow rate, in particular said first range being ±20%; and/or setting the second flow rate of the second pump (70*b*) within a second range of 30% of the optimal second flow rate, in particular said second range being ±20%.

In a 9th aspect according to any one of the preceding two aspects, the optimal first flow rate is comprised between 100 ml/min and 1500 ml/min, and/or wherein the optimal second flow rate is comprised between 100 ml/min and 1500 ml/min.

In a 10th aspect according to any one of the preceding three aspects, the peritoneal dialysis procedure comprises the steps of:

commanding the first flow rate in a range between 100 ml/min and 1500 ml/min commanding the second flow rate in a range between 100 ml/min and 1500 ml/min In a 11th aspect according to any one of the preceding aspects, the peritoneal dialysis procedure comprises a filling procedure to fill the patient abdomen with dialysis fluid through the at least one patient line (28), during the filling procedure said first flow rate being higher than said second flow rate.

In a 12th aspect according to any one of the preceding aspects, the peritoneal dialysis procedure comprises a drainage procedure to remove spent dialysis fluid from the patient abdomen through the at least one patient line, during the drainage procedure said first flow rate being lower than said second flow rate.

In a 13th aspect according to any one of the preceding two aspects, the peritoneal dialysis procedure comprises alternating the filling procedure and the drainage procedure in a cycle. For example, 3 to 5 cycles may be delivered to the patient (e.g., for each night of treatment).

In a 14th aspect according to any one of the preceding aspects, the peritoneal dialysis procedure comprises interposing a dwell time between an end of the filling procedure and a subsequent start of the drainage procedure, said dwell time being comprised between 1 min and 360 min.

In a 15th aspect according to any one of the preceding aspects, the peritoneal dialysis procedure comprises interposing a waiting time between an end of the drainage procedure and a subsequent start of the filling procedure, said waiting time being comprised between 1 min and 20 min.

In a 16th aspect according to any one of the preceding aspects, the first pump is a volumetric pump, in particular the first pump being one of a reciprocating pump, a peristaltic pump, a membrane pump, or a gear pump, a piston pump.

In a 17th aspect according to any one of the preceding aspects, the second pump is a volumetric pump, in particular the second pump being one of a reciprocating pump, a peristaltic pump, a membrane pump, or a gear pump, a piston pump.

In an 18th aspect according to any one of the preceding aspects, the first pump and the second pump includes rotating elements that are movable by rotation, in particular wherein a rotation of the first pump and of the second pump determine respectively the first flow rate and the second flow rate.

In a 19th aspect according to any one of the preceding aspects, the first pump and the second pump are of the same type.

In a 20th aspect according to any one of the preceding aspects, the fluid circuit (in detail the fluid recirculation loop 130) comprises a recirculation portion extending from an outlet of the second pump up to an inlet of the first pump, in particular from the second pump up to the first pump along a fluid direction A defined by the first and second pumps.

It is noted that the recirculation portion (13) does not include (is not directly in fluid communication with) the second end (28b) of the patient line (28).

In a 21st aspect according to any one of the preceding aspects, the fluid direction (A) is defined from the first pump (70a) towards the patient line (28), and from the patient line (28) to the second pump (70b), and in particular from the second pump (70b) towards said recirculation portion (13).

In a 22nd aspect according to any one of the preceding aspects, said recirculation portion comprises a waste container and/or is connected to a discharging line.

In a 23rd aspect according to any one of the preceding aspects, if the first flow rate is smaller than the second flow rate, the waste container fills up and/or the discharging line discharges dialysis fluid.

In a 24th aspect according to any one of the preceding aspects, the delivery line, the withdrawal line and the recirculation portion are fluidly connected each other in series defining part of the fluid recirculation loop (130) (a loop circuit).

In a 25th aspect according to the preceding aspect, the peritoneal dialysis procedure comprises circulating the dialysis fluid into said fluid recirculation loop (130) through the first pump (70a) and the second pump (70b).

In a 26th aspect according to any one of the preceding aspects, the fluid circuit comprises the discharging line (14) connected to the recirculation portion (13), wherein the discharging line extends from the recirculation portion to an (e.g., free) outlet for draining the fluid, in particular the discharging line being connected to the recirculation portion through a three way connector.

In a 27th aspect according to any one of the preceding aspects, the first pump comprises an inlet and an outlet, the first pump being configured to move the dialysis fluid in a direction from the inlet to the outlet.

In a 28th aspect according to any one of the preceding aspects, the second pump comprises an inlet and an outlet, the second pump being configured to move the dialysis fluid in a direction from the inlet to the outlet.

In a 29th aspect according to any one of the preceding two aspects, the outlet of the first pump and the inlet of the second pump face the second end (28b) of the patient line (28).

In a 30th aspect according to any one of the preceding aspects, the at least one patient line comprises:
   a dual lumen patient line, said dual lumen patient line comprising, in particular combining in a single body, a filling line connected to the delivery line and configured to deliver dialysis fluid into the patient abdomen, and a sucking line connected to the withdrawal line and configured to remove fluid from the patient abdomen; or
   a filling line connected to the delivery line and configured to deliver dialysis fluid into the patient abdomen, and a sucking line connected to the withdrawal line and configured to remove fluid from the patient abdomen, wherein the filling line is distinct from the sucking line.

In a 31st aspect according to the preceding aspect, the patient line comprises the dual lumen patient line, and wherein the fluid circuit comprises a three-way connector comprising a first way connected to an end of the delivery line, a second way connected to the second end of the patient line, and a third way connected to an end of the withdrawal line.

In a further depending aspect according to any one of the preceding aspects, the at least one patient line comprises a single lumen line for alternatively sending and withdrawing dialysis fluid into and from the patient's abdomen.

In a 32nd aspect according to any one of the preceding aspects, the fluid circuit (10) comprises a first flow meter (81) configured to measure a current first flow rate provided by the first pump (70a), the first flow meter (81) being arranged in series with the first pump (70a) so that a same fluid flow rate flows through the first pump (70a) and the first flow meter (81), in particular wherein the first flow meter (81) is arranged on the recirculation portion (13) upstream the first pump (70a) or on the delivery line (11).

In a further aspect according to the previous aspect, the first flow meter (81), when on the delivery line (12), is upstream the second end (28b) of the patient line (28).

In a further aspect according to the previous two aspects, the first flow meter (81), when on the recirculation portion (13), is downstream the discharging line (14).

In a 33rd aspect according to any one of the preceding aspects, the fluid circuit (10) comprises a second flow meter (82) configured to measure a current second flow rate provided by the second pump (70b), the second flow meter (82) being arranged in series with the second pump (70b) so that a same fluid flow rate flows through the second pump (70b) and the second flow meter (82), in particular wherein the second flow meter (82) is arranged on the recirculation portion (13) downstream the second pump (70b) or on the withdrawal line (12).

In a further aspect according to the previous aspect, the second flow meter (82), when on the delivery line (12), is downstream the second end (28b) of the patient line (28).

In a further aspect according to the previous two aspects, the second flow meter (82), when on the recirculation portion (13), is upstream the discharging line (14).

In a 34th aspect according to any one of the preceding aspects, the first flow rate of the first pump flows through the first flow meter during an operating condition.

In a 35th aspect according to any one of the preceding aspects, the second flow rate of the second pump flows through the second flow meter during an operating condition.

In a 36th aspect according to any one of the preceding aspects, the peritoneal dialysis procedure comprises:
   calculating/determining the current first flow rate measured by the first flow meter (81);
   calculating/determining the current second flow rate measured by the second flow meter (82);
   calculating/determining a current exchange parameter value based on a difference between the current first flow rate and the current second flow rate, said current exchange parameter value representing the current exchange flow rate of dialysis fluid with the patient;
   comparing the current exchange parameter value with a desired exchange parameter value;
   based on this comparison, and in particular if a difference between the current exchange parameter value and the desired exchange parameter value overcomes a predefined threshold, adjusting a flow rate of the first pump (70a) and/or of the second pump (70b), in particular adjusting a difference in flow rate between the first pump (70a) and the second pump (70b).

In a 37th aspect according to any one of the preceding aspects, the filling procedure comprises the steps of:
   calculating a filling fluid amount of dialysis fluid delivered to the patient's abdomen from a beginning of the filling procedure based on a difference between the first flow rate and the second flow rate, in particular based on a difference between the current first flow rate and the current second flow rate, and optionally further based on a time duration of the filling procedure;

comparing said filling fluid amount with a (maximum) filling fluid amount threshold;

commanding a stop of the first pump (70a) and of the second pump (70b) when said filling fluid amount overcomes the (maximum) filling fluid amount threshold.

In a 38th aspect according to any one of the preceding aspects, the drainage procedure comprises the steps of calculating a drainage fluid amount of dialysis fluid removed from the patient's abdomen from a beginning of the drainage procedure based on a difference between the first flow rate and the second flow rate, in particular based on a difference between the current first flow rate and the current second flow rate, optionally further based on a time duration of the drainage procedure;

comparing said drainage fluid amount with a (maximum) drainage fluid amount threshold;

commanding a stop of the first pump (70a) and of the second pump (70b) when said drainage fluid amount overcomes the (maximum) drainage fluid amount threshold.

Drainage and filling amount threshold may be equal one to the other.

Further, different drainage and filling amount thresholds may be used for different treatment cycles.

In a 39th aspect according to any one of the preceding aspects, the fluid circuit comprises a dialysis fluid heater configured to heat up the dialysis fluid, in particular wherein said dialysis fluid inline heater is arranged in the recirculation portion of the fluid circuit.

Preferably, the heater (56) is arranged in the fluid recirculation loop (130).

In a 40th aspect according to any one of the preceding aspects, the fluid circuit comprises an air trap configured to remove air bubbles from the dialysis fluid, in particular the air trap being arranged on the recirculation portion of the fluid circuit.

Preferably, the air trap (60)) is arranged in the fluid recirculation loop (130) e.g., downstream the heater (56).

In a 41st aspect according to any one of the preceding aspects, the fluid circuit defines a loop circuit for recirculating the dialysis fluid (fluid recirculation loop 130), said loop circuit comprising at least the delivery line and the withdrawal line fluidly connected each other to define said loop circuit, the loop circuit further comprising in particular the recirculation portion.

In a 42nd aspect according to the preceding aspect, said loop circuit comprises at least the first pump, the second pump.

In a 43rd aspect according to any one of the preceding aspects, the loop circuit comprises the patient line.

In a 44th aspect according to any one of the preceding aspects, the loop circuit comprises the filling line and the sucking line of the patient line.

In a 45th aspect according to any one of the preceding aspects, the loop circuit further comprises a dialysis fluid heater configured to heat up the dialysis fluid.

In a 46th aspect according to any one of the preceding aspects, the loop circuit further comprises an air trap configured to remove air bubbles from the dialysis fluid stream.

In a 47th aspect according to any one of the preceding aspects, the fluid circuit comprises a discharging line extending from an inlet connected to loop circuit, and an outlet for the spent dialysis fluid.

In a 48th aspect according to any one of the preceding aspects, the delivery line is interposed between the first pump and the second end of the patient line.

In a 49th aspect according to any one of the preceding aspects, the withdrawal line is interposed between the second pump and the second end of the patient line.

In a 50th aspect according to any one of the preceding aspects, the fluid circuit further comprises a preparation assembly configured to prepare dialysis fluid to be supplied to the patient according to a predefined recipe.

In a 51st aspect according to the preceding aspect, said preparation assembly comprises one or more supply lines for connection to a respective fluid source, in particular a solution bag, containing dialysis fluid or a solution.

In a 52nd aspect according to any one of the preceding aspects, said one or more supply lines are configured, in particular during the filling procedure, to deliver fluid to the recirculation portion (13) of the fluid circuit (10).

In a 53rd aspect according to any one of the preceding aspects, said one or more supply lines comprise at least a first supply line and a second supply line respectively connected or configured to connect to a first fluid source, i.e. a first solution bag, and to a second fluid source, i.e. a second solution bag.

In a 54th aspect according to any one of the preceding aspects, the preparation assembly is configured to deliver, and also in particular mix, the solution of the first solution bag and the solution of the second solution bag in the loop circuit.

In a 55th aspect according to any one of the preceding aspects, the preparation assembly, in particular the one or more supply lines, is connected to the recirculation portion of the fluid circuit.

In a 56th aspect according to any one of the preceding aspects, the one or more supply lines are connected to the loop circuit of the fluid circuit.

In a 57th aspect according to any one of the preceding aspects, the fluid circuit (10) comprises at least one supplying valve (54a, 54b, 54c, 154) fluidly interposed between the preparation assembly (90), in particular between the one or more supply lines, and the recirculation portion (13) of the fluid circuit (10).

In a 58th aspect according to any one of the preceding aspects, the at least one supplying valve (54a, 54b, 54c, 154) is fluidly interposed between the preparation assembly (90), in particular between the one or more supply lines, and the loop circuit.

In a 59th aspect according to any one of the preceding aspects, the at least one supplying valve (54a, 54b, 54c, 154) is movable between an open position, wherein fluid is allowed to move from the one or more supply lines to the recirculation portion (13) or to the loop circuit, and a close position wherein fluid passage is prevented between the one or more supply lines and the recirculation portion (13) or the loop circuit.

In a 60th aspect according to any one of the preceding aspects, during the filling procedure, the peritoneal dialysis procedure (200) comprises a step, performed by the control unit (100), to command the at least one supplying valve (54a, 54b, 54c, 154) in the open position to allow fluid to move from the preparation assembly (90) to the recirculation portion (13) or to the loop circuit of the fluid circuit (10).

In a 61st aspect according to any one of the preceding aspects, the fluid circuit comprises a discharging valve movable between an open position, wherein fluid is allowed to be discharged through the discharging line, and a close position wherein fluid passage through the discharging line is prevented.

In a 62nd aspect according to the preceding aspect, during the drainage procedure, the peritoneal dialysis procedure comprises a step, performed by the control unit, to command the discharging valve in the open position.

In a 63rd aspect according to any one of the preceding aspects, during the filling procedure, the peritoneal dialysis procedure (200) comprises a step, performed by the control unit (100), to command:

the at least one supplying valve (54a, 54b, 54c, 154) in the open position; and the discharging valve (54i) in the close position.

In a 64th aspect according to any one of the preceding aspects, during the drainage procedure, the peritoneal dialysis procedure (200) comprises a step, performed by the control unit (100), to command:

the at least one supplying valve (54a, 54b, 54c, 154) in the close position; and the discharging valve (54i) in the open position.

A 65th aspect is directed to a peritoneal dialysis apparatus (20) comprising a housing (22), said housing (22) carrying the fluid circuit (10) according to any one of the preceding aspects and claims.

Notably in the FIGS. 2-6, darkened valves are open at least at some point within the sequence, while the empty valves are in the close position. The arrows show the direction A of fresh or spent dialysis fluid.

DETAILED DESCRIPTION

Figure 1:
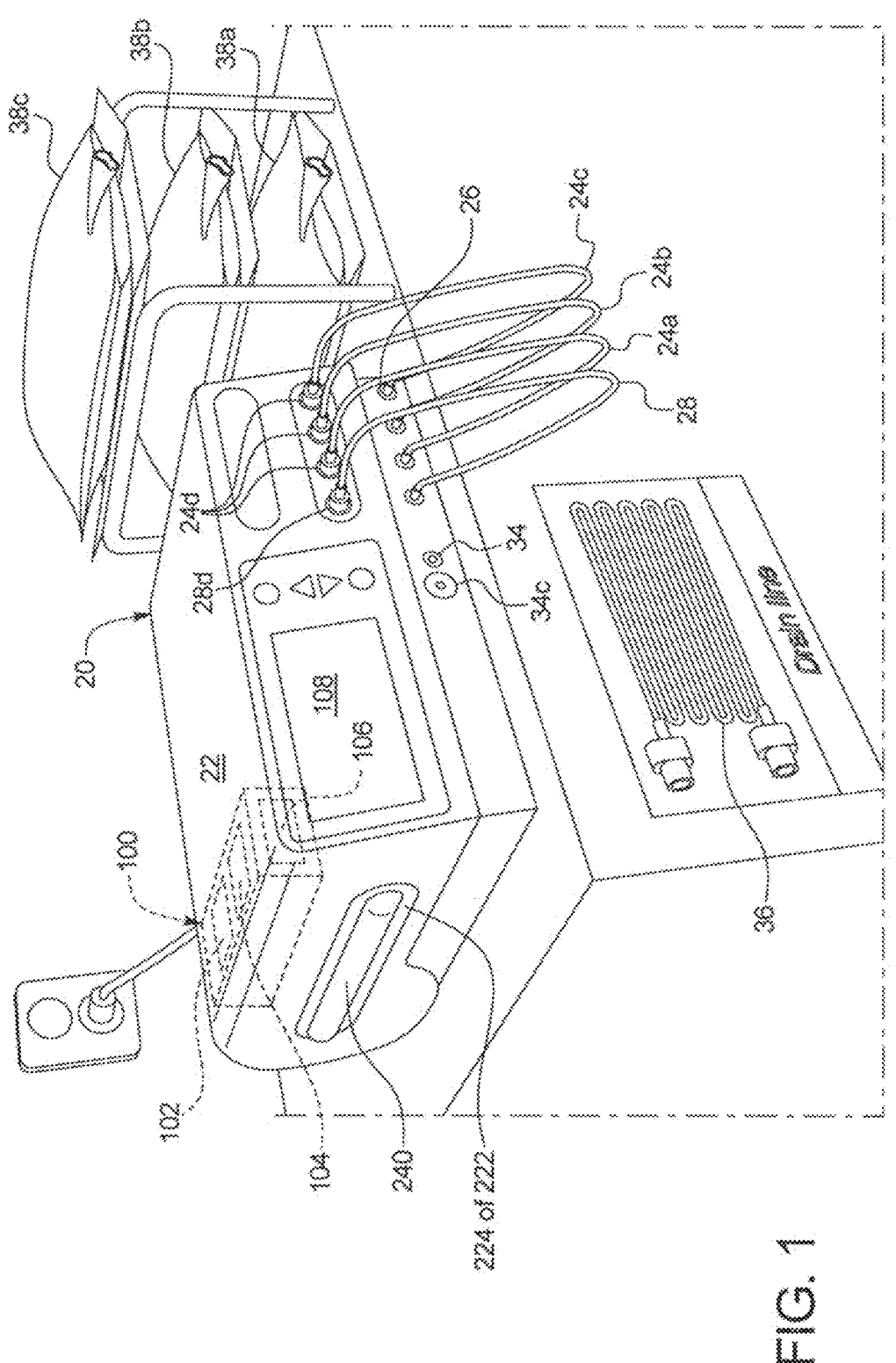
FIG. 1 is a perspective view of one embodiment of a peritoneal dialysis apparatus according to the present invention.

The following disclosure is directed to a peritoneal dialysis apparatus 20 comprising a fluid circuit for performing a peritoneal dialysis treatment to a patient. FIG. 1 depicts a representative embodiment of a peritoneal dialysis apparatus 20 comprising the fluid circuit 10 of the present invention.

In particular, peritoneal dialysis apparatus 20 includes a housing 22 defining an internal volume carrying at least part of the fluid circuit 10 for carrying the peritoneal dialysis treatment. The fluid circuit 10 may comprise PD fluid lines 24a, 24b, 24c extending outwardly from apertures 26 defined or provided by the housing 22. Apertures 26 may be fitted with grommets or be otherwise sealed, such that dust, fluids, and other substances cannot enter housing 22 from the environment.

FIG. 1 further illustrates that a patient line 28 also extends from housing 22 of the apparatus 20 via a sealed aperture 26, e.g., fitted with a grommet. Patient line 28, which is typically longer than PD fluid lines 24a to 24c, may be coiled or rolled up within housing via a spool or hose reel 110 when patient line 28 is not connected to a patient for treatment. Patient line 28 may also be coated with a non-sticking or smooth coating to prevent dirt from collecting on the patient line over time. The patient line 28 may be reusable or disposable.

The patient line 28 extends between a first end 28a, configured to connect to the patient's abdomen, and a second end 28b.

The patient line 28 may comprise a dual lumen patient line combining in a single body a filling line configured to deliver dialysis fluid into the patient abdomen, and a sucking line configured to remove fluid from the patient abdomen. System 10 also includes a patient line connector 32b. Patient line connector 32b includes an internal lumen, e.g., a U-shaped lumen, which directs fresh or used dialysis fluid from one PD fluid lumen of dual lumen reusable patient line 28 into the other PD fluid lumen. Alternatively, the patient line may comprise a filling line and a sucking line distinct from each other, defining two distinct lines. Also a patient line including one single lumen is included within the described embodiments; the single lumen line is used for alternatively sending and withdrawing dialysis fluid into and from the patient's abdomen. Cleaning cartridge 240 is also illustrated in FIG. 1 showing that it may be slid conveniently into a slot 224 of housing 222 of cycler 20.

The fluid circuit 10 further comprises a delivery line 11 configured to deliver dialysis fluid towards the patient line 28. The delivery line 11 is fluidly and directly connected to the second end 28b of the patient line 28b. In particular the delivery line 11 may be connected to the filling line of the patient line 28 to deliver dialysis fluid to the patient's abdomen. The delivery line 11 extends in length between a first end 11a and a second end 11b: the second end 11b of the delivery line 11 is connected to the second end 28b of the patient line 28, so that fluid may flow from the delivery line 11 to the patient line 28 to supply dialysis fluid to the patient. In particular the second end 11b of the delivery line 11 is connected to the filling line of the patient line 28, The delivery line 11 may be a reusable line arranged within the housing 22 of the apparatus 20. In particular the delivery line 11 may be made of rigid or flexible material.

The fluid circuit 10 further comprises a withdrawal line 12 configured to withdraw spent dialysis fluid from the patient line 28. The withdrawal line 12 extends in length between a first end 12a and a second end 12b. The second end 12b of the withdrawal line 12 is connected to the second end 28b of the patient line 28, so that fluid may flow from the patient line 28 to the withdrawal line 12 to remove dialysis fluid from the patient. In particular the second end 12b of the withdrawal line 12 is connected to the sucking line of the patient line 28. The withdrawal line 12 may be a reusable line arranged within the housing 22 of the apparatus 20. In particular the withdrawal line 12 may be made of rigid or flexible material.

Notably, the second end 12b of the withdrawal line 12, the second end 11b of the delivery line 11, and the second end 28b of the patient line 28 are connected each other defining a three way connection.

The fluid circuit 10 further comprises a first pump 70a arranged on the delivery line 11, and configured to supply fresh dialysis fluid towards the patient line 28. The first pump 70*a* comprises an inlet and an outlet, wherein the first pump 70*a* is configured to move the dialysis fluid in a direction from the inlet towards the outlet. The outlet of the first pump 70*a* is connected to the first end 11*a* of the delivery line 11, to move the dialysis fluid into the delivery line 11 and towards the patient line 28. Thus the delivery line 11 is interposed between the outlet of the first pump 70*a* and the second end 28*b* of the patient line 28. Notably, the outlet of the first pump 70*a* faces the second end 28*b* of the patient line 28.

The first pump 70*a* may be a volumetric pump: in particular the first pump may be one of a reciprocating pump, a peristaltic pump, a membrane pump, or a gear pump, and a piston pump.

The first pump may include elements that are movable by rotation, so that a rotation of the first pump 70*a* determines a flow rate of the dialysis fluid towards the patient line 28.

The first pump 70*a* may be configured to work at an optimal first flow rate range between 100 ml/min 1500 ml/min. The optimal flow rate range of the first pump 70*a* may define a best efficiency working condition of the first pump.

The fluid circuit 10 further comprises a second pump 70*b* arranged on the withdrawal line 12, and configured to suck dialysis fluid from the patient line 28 into the withdrawal line 12. The second pump 70*b* comprises an inlet and an outlet, wherein the second pump 70*b* is configured to move the dialysis fluid in a direction from the inlet to the outlet. The inlet of the second pump 70*b* is connected to the first end 12*a* of the withdrawal line 12: thus the withdrawal line 12 is interposed between the second end 28*b* of the patient line 28 and the inlet of the second pump 70*b*. Notably, the inlet of the second pump 70*b* faces the second end 28*b* of the patient line 28.

The second pump 70*b* may be a volumetric pump: in particular the second pump 70*b* may be one of a reciprocating pump, a peristaltic pump, a membrane pump, or a gear pump, and a piston pump. Optionally the first pump 70*a* and the second pump 70*b* are of the same type, for example both gear pumps.

The second pump 70*b* may include elements that are movable by rotation, so that a rotation of the second pump 70*b* determines a flow rate of the dialysis fluid from the patient line 28 towards the withdrawal line 12.

The second pump 70*b* may be configured to work at an optimal second flow rate range between 100 ml/min and 1500 ml/min. The optimal second flow rate range of the second pump 70*b* may define a best efficiency working condition of the second pump 70*b*.

When mentioned pumps are driven within their optimal flow rates, pump accuracy is improved as well as pump noise is reduced.

The fluid circuit 10 further comprises a recirculation portion 13 interposed between the second pump 70*b* and the first pump 70*a* along a fluid direction A defined by the first pump and the second pump. In particular the recirculation portion 13 extends from the outlet of the second pump 70*b* up to the inlet of the first pump 70*a*. In particular the fluid direction A is defined from the first pump 70*a* towards the patient line 28, and from the patient line 28 to the second pump 70*b*, and from the second pump 70*b* towards the recirculation portion 13.

The recirculation portion 13 may be a reusable line arranged within the housing 22 of the apparatus 20. In particular the recirculation portion 13 may be made of rigid or flexible material.

The recirculation portion 13 may comprise a waste container. For example the recirculation portion 13 may comprise an air trap 60 configured to remove air bubbles from the dialysis fluid flowing into the fluid circuit. The air trap 60 may be arranged upstream to the first pump 70*a*, and downstream to the second pump 70*b* according to the fluid direction A. Upper and/or lower level sensors 62*a* and 62*b* may be provided to the air trap to monitor the fluid level within the air trap 60. Upper and/or lower level sensors 62*a* and 62*b* may be operatively connected to the control unit 100, so that the control unit may be configured to trigger an action or emit and alarm in case the fluid level exceeds the upper level or the lower level.

The fluid circuit 10 may further comprise a fluid heater 56 configured to heat up the dialysis fluid at a temperature compatible with the patient (e.g., 37° C.). The fluid heater 56 may be arranged on the recirculation portion 13. For example the fluid heater 56 may be arranged upstream to the air trap 60.

Dialysis fluid heater 56 may be electrically actuated in one embodiment and is, for example, a resistive heater having a reusable heater body that accepts PD fluid for treatment and disinfection heating. Heater 56 is able to heat PD fluid from room temperature or colder (e.g., if the PD fluid is stored in a cold environment) to body temperature, e.g., 37° C., at a flowrate of at least 200 milliliters (ml)/minute (lower flowrates may also be achieved, e.g., for children or infants). Alternatively, the apparatus 20 comprises an external heater configured to receive the fluid circuit to heat up the dialysis fluid therein.

The fluid circuit 10 may comprise a temperature sensor 58*a* located adjacent to the fluid heater 56, e.g., downstream from the heater to provide feedback for temperature control. If desired, a second temperature sensor (not illustrated) may be provided upstream from heater 56 to enable the incoming temperature of fresh dialysis fluid to be taken into account for the heating algorithm or routine, that is, to provide feedforward control, which stabilizes and speeds the responsiveness of the overall heating control. The second sensor may also provide useful information for calculating disinfection dose values, e.g., AO values, for use during disinfection.

A flow switch 80, outputting to control unit 100, may be arranged on the recirculation portion 13 of the fluid circuit 10. Flow switch 80 is set to trip or output at a designated low flowrate, which is indicative of one of containers or bags 38*a* to 38*c* becoming empty, and which may also be used to ensure that fresh PD fluid is flowing through inline heater 56 when the heater is powered for fluid heating.

The fluid circuit may further comprise a first flow meter 81 configured to measure a flow rate provided by the first pump 70*a*. The first flow meter 81 may be arranged in series to the first pump 70*a* so that a same fluid flow rate flows through the first pump 70*a* and the first flow meter 81. In particular the first flow meter 81 may be arranged on the delivery line 11, between the first pump 70*a* and the second end 28*b* of the patient line 28. Alternatively, the first flow meter 81 may be arranged on the recirculation portion 13 upstream the first pump 70*a*. The first flow meter 81 may be arranged close to the first pump, either upstream or downstream to the first pump 70*a*, for example at a maximum fluid distance from the first pump 70*a* comprised between 1 cm and 5 cm.

The fluid circuit may further comprise a second flow meter 82 configured to measure a flow rate provided by the second pump 70*b*. The second flow meter 82 may be arranged in series with the second pump 70*b* so that a same fluid flow rate flows through the second pump 70*b* and the second flow meter 82. In particular the second flow meter 82 may be arranged on the withdrawal line 12, between the second pump 70*b* and the second end 28*b* of the patient line 28. Alternatively, the second flow meter 82 may be arranged on the recirculation portion 13 downstream the second pump 70*b*. The second flow meter 82 may be arranged close to the second pump 70*b*, either upstream or downstream to the second pump 70*b*, for example at a maximum fluid distance from the second pump 70*b* comprised between 1 cm and 5 cm.

The fluid circuit 10 may comprise a conductivity sensor 74 to detect the conductivity of fresh PD fluid to make sure that it is of a prescribed type, e.g., of a prescribed glucose or dextrose level. Conductivity sensor 74 may alternatively or additionally be used to detect the conductivity of the fresh PD fluid to make sure that it has been mixed correctly, e.g., if an online PD fluid source is connected instead to one of the PD fluid lines 24*a* to 24*c*. Conductivity sensor 74 may alternatively or additionally be used to detect the conductivity of the used PD fluid to assess treatment effectiveness and/or to look for patient disease, such as peritonitis.

The conductivity sensor 74 may be arranged adjacent to the first pump 70*a*, upstream or downstream with respect to the first pump 70. According to the embodiment of the attached figures, the conductivity sensor 74 may be interposed between the first pump 70*a* and the patient line 28. In particular the conductivity sensor 74 may be arranged downstream of the first pump 70*a*. Alternatively, the conductivity sensor 74 may be arranged upstream of the first pump 70*a*, in particular between the air trap 60 and an inlet of the first pump 70*a*.

A temperature sensor 58*b* may be provided close to the conductivity sensor 74, so that the conductivity reading from the sensor may be temperature compensated.

The fluid circuit 10 defines a loop circuit for recirculating the dialysis fluid. In particular the delivery line 11, the withdrawal line 12 and the recirculation portion 13 define in combination the loop circuit. The dialysis fluid flows in the fluid direction A within the loop circuit. In particular the dialysis fluid may recirculate within the loop circuit from the delivery line 11, to the withdrawal line 12, and into the recirculation portion 13. In more detail, the dialysis fluid may recirculate within the loop circuit from the delivery line 11, into the filling line of the patient line 28, then back into the sucking line of the patient line 28 to the withdrawal line 12, and then into the recirculation portion 13 to return at the inlet of the first pump 70*a*.

The loop circuit further comprises the first pump 70*a*, the second pump 70*b*, and the second end 28*b* of the at least one patient line 28. Notably, the loop circuit further comprises the patient line 28. Furthermore, the loop circuit may include both the first flow meter 81 and the second flow meter 82. In addition, the loop circuit may include the heater 56 and/or the temperature sensor 58*a*. The loop circuit may also include the air trap 60. The loop circuit may also include the conductivity sensor 74.

Figure 2:
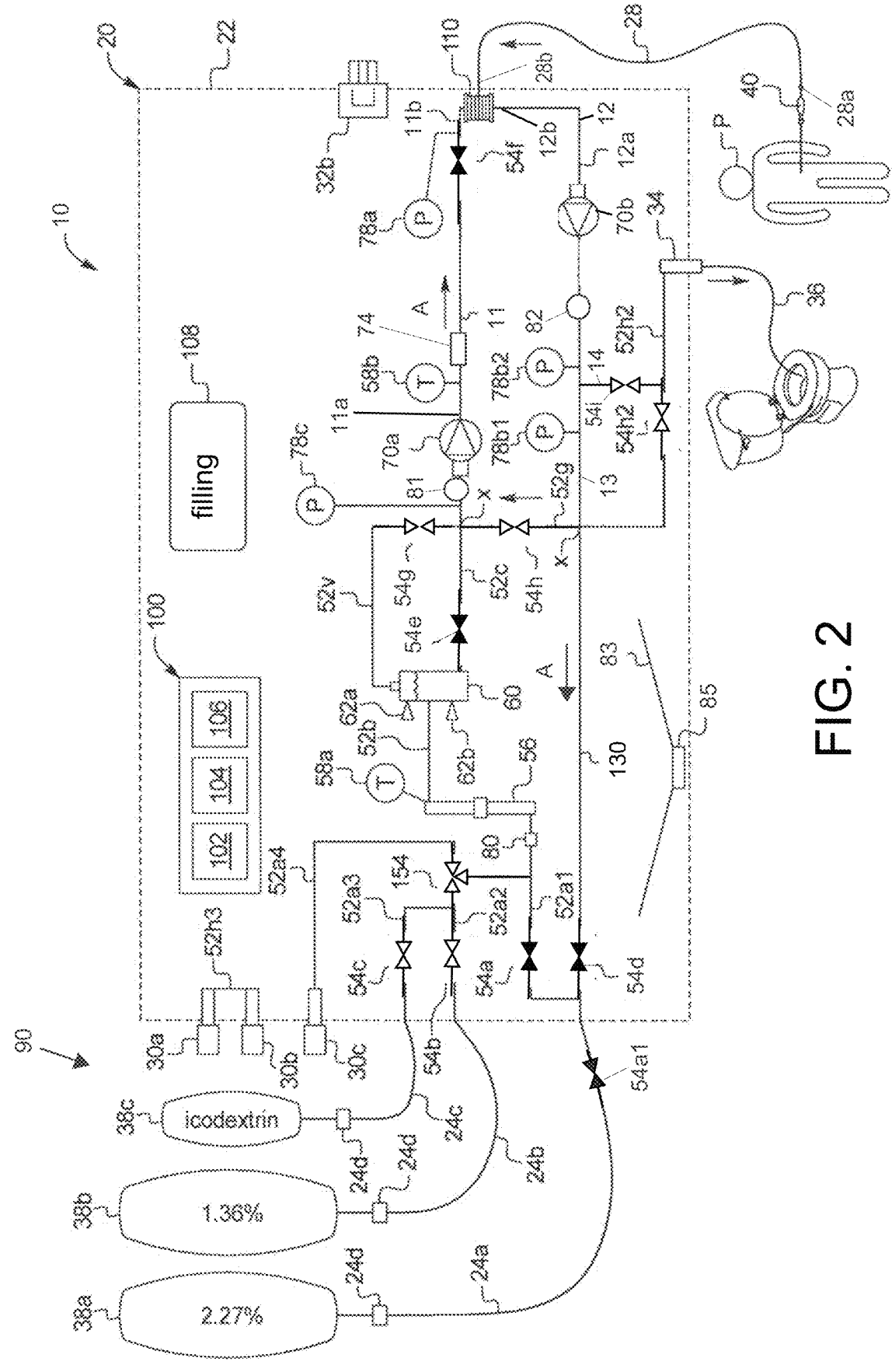
FIGS. 2 and 3 are schematic views of a fluid circuit of the peritoneal dialysis apparatus according to an embodiment of the present invention during a filling process.
Figure 3:
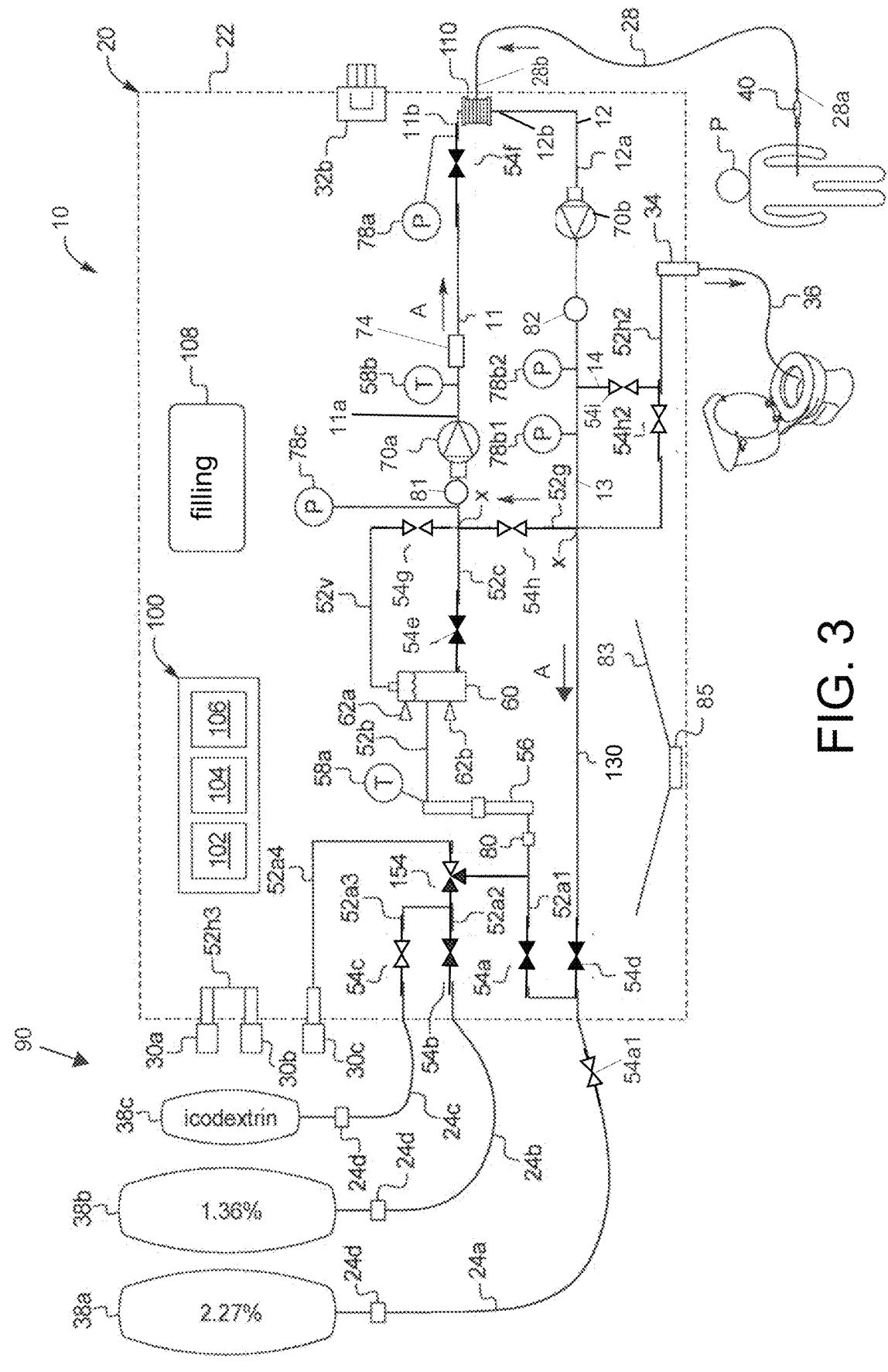
Figure 4:
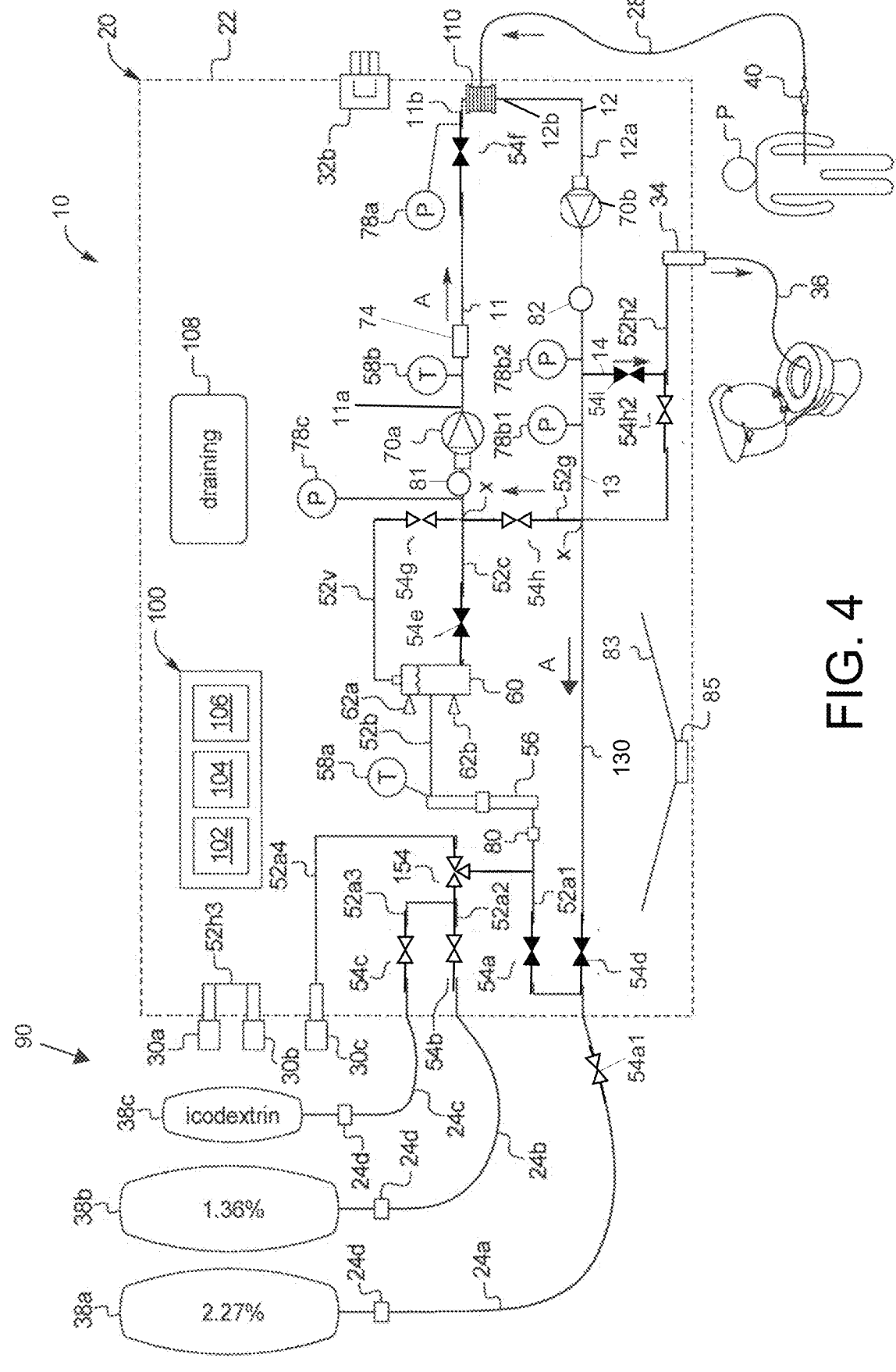
FIG. 4 is a schematic view of a fluid circuit of the peritoneal dialysis apparatus according to an embodiment of the present invention during a draining process.

According to the embodiment of FIGS. 2-4, the loop circuit comprises the first pump 70*a*, the second pump 70*b*, the delivery line 11, the withdrawal line 12, the recirculation portion 13, the heater 56, the air trap 60 and, optionally, the first and the second flow meters 81, 82.

Figure 5:
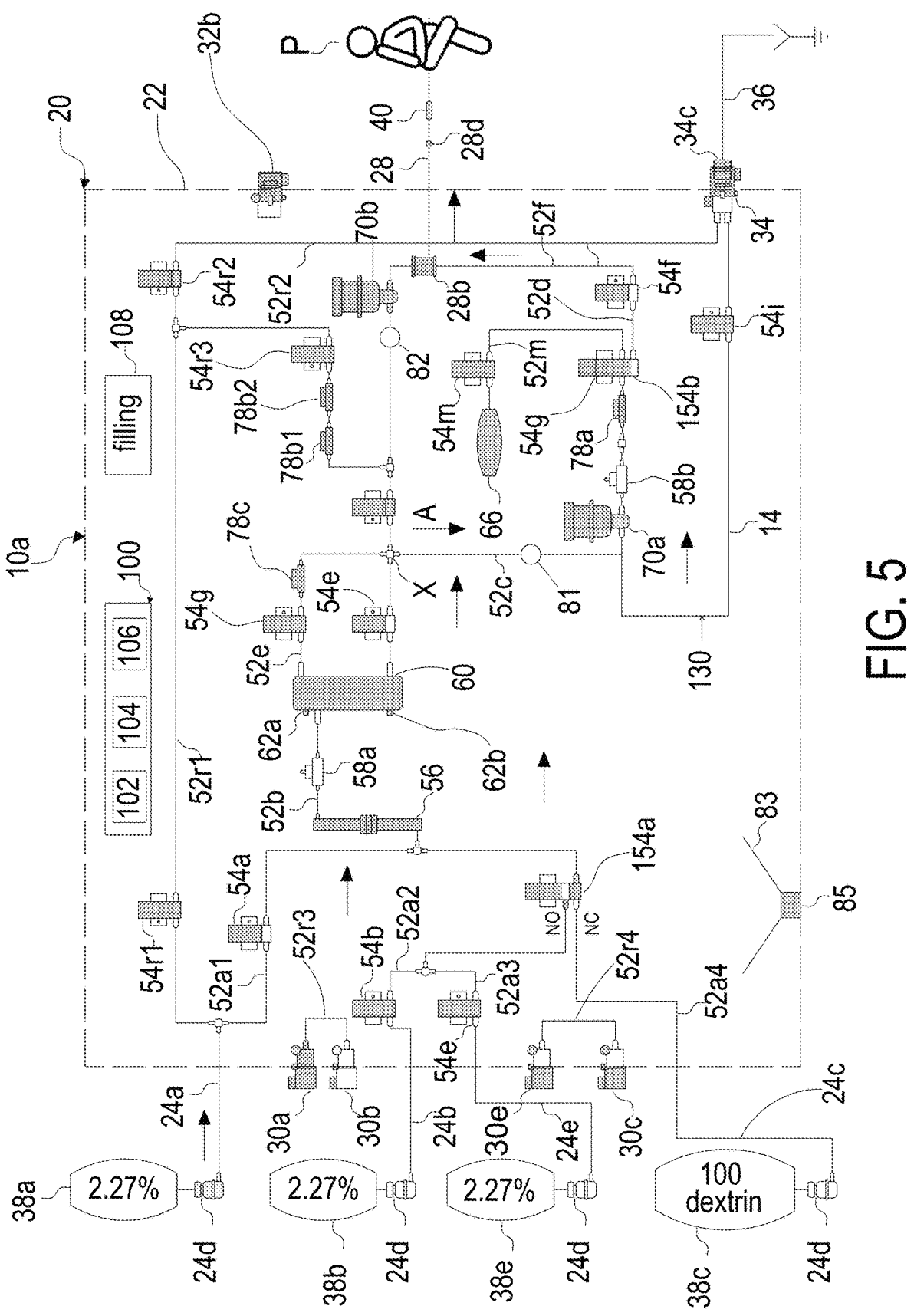
FIG. 5 is a schematic view of a fluid circuit of the peritoneal dialysis apparatus according to a further embodiment of the present invention during a filling process.
Figure 6:
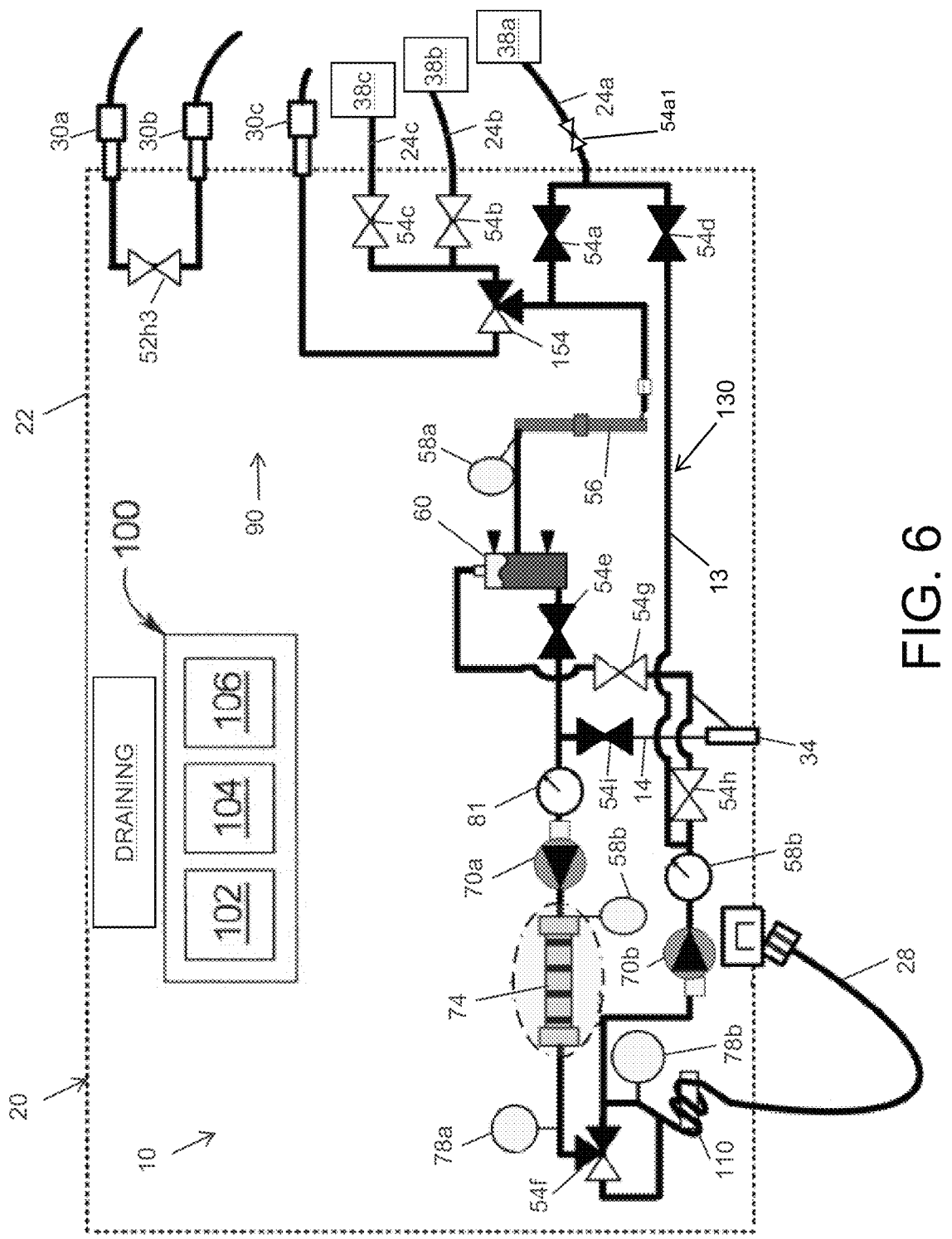
FIG. 6 is a schematic view of a fluid circuit of the peritoneal dialysis apparatus according to another embodiment of the present invention during a draining process.
Figure 7:
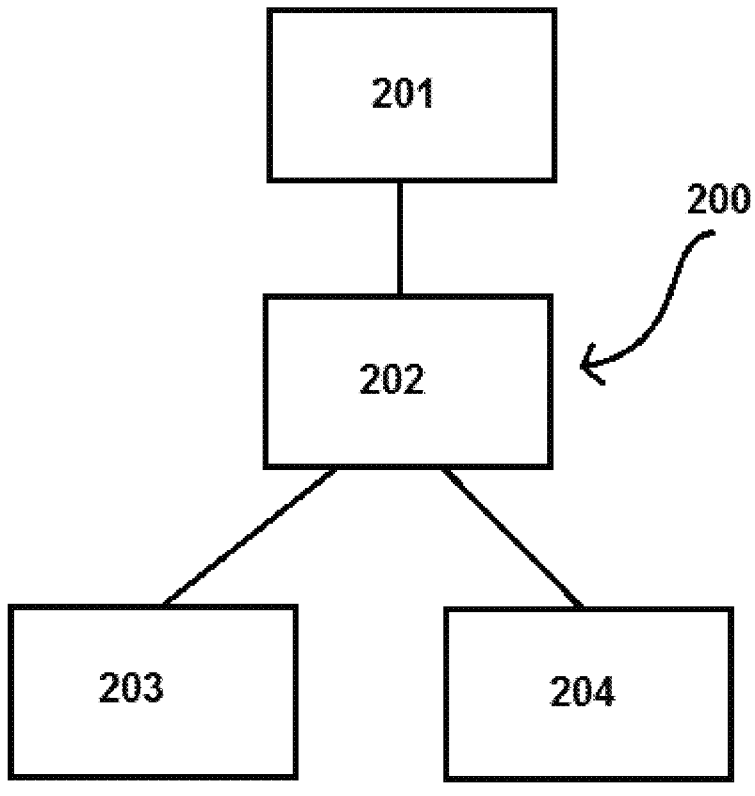
FIG. 7 is a flowchart of the main steps of the peritoneal dialysis procedure.

According to the further embodiment of FIG. 5, the loop circuit comprises the first pump 70*a*, the second pump 70*b*, the delivery line 11, the withdrawal line 12, the recirculation portion 13 and, optionally, the first and the second flow meters 81, 82: according to this embodiment of FIG. 5, the air trap 60 and the heater 56 are excluded from the loop circuit.

The fluid circuit 10 may also comprise a discharging line 14 configured to discharge spent dialysis fluid. The discharging line 14 extends in length between an inlet 14*a* and an outlet, so that the dialysis fluid is discharged in a direction from the inlet to the outlet of the discharging line 14.

Alternatively, the discharging line 14 may be connected to the recirculation portion 13, as shown in the attached figures. In particular the inlet of the discharging line 14 may be arranged upstream to the first pump 70*a* and downstream to the second pump 70*b*. For example, the inlet of the discharging line 14 may be arranged between the air trap 60 and the inlet of the first pump 70*a*.

More in general, the inlet of the discharging line 14 is connected to the loop circuit of the fluid circuit 10.

A drain line connector 34 may be provided at the outlet 14*b* of the discharging line 14: the drain line connector 34 may be releasably covered by a moveable, e.g., rotatable or slideable, cover 34*c*. Drain line connector 34 may receive a disposable drain line 36 for treatment, which may run to a drain container or bag or to a house drain. In an alternative embodiment, drain line 36 is reusable and is connected to a disinfection loop.

The fluid circuit 10 further comprises a preparation assembly 90 configured to prepare dialysis fluid according to a predefined recipe to be supplied to the patient. The preparation assembly comprises one or more supply lines 24*a*, 24*b*, 24*c*, for connection to a respective fluid source, i.e. one or more a solution bags 38*a*, 38*b*, 38*c*, containing dialysis fluid, or a solution.

Distal ends 24*d* of PD fluid lines 24*a* to 24*c* may be color coded and/or keyed to match a colored or keyed connector of a dedicated PD fluid container or bag 38*a* to 38*c*. The containers or bags may hold, e.g., different dextrose or glucose level dialysis fluids, such as 1.36% glucose dialysis fluid, 2.27% glucose dialysis fluid, 3.86% glucose dialysis fluid and/or a last bag of a different formulation of PD fluid, for example, icodextrin.

It should be appreciated that any number of PD fluid lines and PD fluid containers or bags may be provided, including a single PD fluid line and PD fluid container or more than one PD fluid lines and PD fluid containers, such as two, three or four. In a further alternative embodiment, PD fluid containers or bags 38*a* to 38*c* are replaced by an online PD fluid generation source, which connects to and communicates fluidly with a single PD fluid line. In a further alternative embodiment, any of the apparatus described herein are configured to operate with either prefilled PD fluid containers or bags 38*a* to 38*c* or an online PD fluid generation source. For example, the apparatus described herein may be provided with an additional port such that the apparatus may be docked or connected to an online PD fluid producing device. Here, the PD apparatus may be released or disconnected from the online PD fluid generation source if the patient wants to travel or if the online source is under repair. The patient is provided with a stock of PD fluid bags, allowing treatment to still be performed. The set of PD fluid containers or bags or the online PD fluid generation source generally define, at least in part, a fluid preparation assembly.

In particular the supply lines 24*a*, 24*b*, 24*c* are connected to the recirculation portion 13 of the fluid circuit, so that the fluid solutions delivered from the fluid sources 38*a*, 38*b*, 38*c* may enter the loop circuit. In an embodiment, the supply lines 24a, 24b, 24c may be connected to the recirculation portion 13 upstream to the heater 56, and/or upstream to the air trap 60.

As depicted in the attached figures, the preparation assembly comprises a first supply line 24a and a second supply line 24b respectively connected or configured to connect to a first fluid source 38a, i.e. a first solution bag 38a, and to a second fluid source 38b, i.e. a second solution bag 38b. The preparation assembly is configured to deliver and mix the solution of the first solution bag 38a and the solution of the second solution bag 38b in the loop circuit.

System 10 includes disinfection connectors 30a to 30c for connecting to distal ends 24d of reusable PD fluid lines 24a to 24c, respectively, during disinfection. A third disinfection tubing or line 52h3 extends between disinfection connectors 30a and 30b for use during disinfection.

It is contemplated for any of reusable or disposable PD fluid lines 24a to 24c, reusable or disposable patient line 28, disinfection connectors 30a to 30c, patient line connector 32a, drain line connector 34, drain line 36, PD fluid containers or bags 38a to 38c and patient line filter set 40 to be made of any one or more plastic, e.g., polyvinylchloride ("PVC") or a non-PVC material, such as polyethylene ("PE"), polyurethane ("PU"), polyetheretherketone ("PEEK") or polycarbonate ("PC"). Certain of the components, such as disinfection connectors 30a to 30c, may be made of, e.g., stainless steel or titanium.

The fluid circuit 10 may comprise a first pressure sensor 78a located in proximity to (e.g., upstream of) the patient line 28 to enable positive, fresh PD fluid fill pressures to be monitored and controlled. A second pressure sensor 78b may be located in proximity to (e.g., downstream of) the patient line 28 to enable negative, used PD fluid drain pressures to be monitored and controlled. The second pressure sensor 78b may comprise pressure sensors 78b1 and 78b2, one for control and the other for safety.

Optionally, the fluid circuit 10 may comprise a pressure sensor 78c upstream of the first pump 70a. Measuring the suction pressure of first pump 70a may help control unit 100 to more accurately determine pump volume. For example, the output of certain piston pumps is dependent on inlet pressure. Another use for pressure sensor 78c is to determine if a currently used container or bag 38a to 38c has or is near empty.

The fluid circuit 10 may comprise a number of valves configured to allow or prevent passage of the dialysis fluid.

At least one supplying valve 54a, 54b, 54c, 154 may be fluidly interposed between the preparation assembly 90, in particular between the one or more supply lines 24a, 24b, 24c, and the recirculation portion 13. In particular the at least one supplying valve 154 is fluidly interposed between the preparation assembly 90, in particular between the one or more supply lines, and the loop circuit.

In one embodiment, the at least one supplying valve comprises a main valve 154 fluidly interposed between the second supply line 24b and the recirculation circuit 13, and between the third supply line 24c and the recirculation circuit. In particular the second supply line 24b and the third supply line 24c may converge in a common line leading to the main valve 154, so that the latter is fluidly interposed between this common line and the recirculation portion 13. Therefore, the main valve 154, when arranged in an open position, allows the substance housed in the second and in the third bags 38b, 38c to be delivered into the recirculation portion 13 of the fluid circuit, in particular in the loop circuit.

Furthermore, according to an embodiment not shown in the attached figures, the main valve 154 may be also fluidly interposed between the first supply line 24a and the recirculation circuit 13.

The at least one supplying valve may also comprise a first valve 54a, a second valve 54b and a third valve 54c arranged respectively on the first supply line 24a, the second supply line 24b, and the third supply line 24c. The second valve 54b and the third valve 54c may be arranged upstream of the main valve 154 according to the fluid direction from the bags 38b, 38c to the recirculation portion 13. Three-way valve 154 is likely toggled between supply lines 52a2, 52a3 and disinfection connector line 52a4 in any valve open versus toggle arrangement.

In an embodiment, the first valve 54a may be arranged directly on the recirculation portion 13, namely on the loop circuit. In this case, the first valve 54a may be arranged downstream of a connection point between the first supply line 24a and the recirculation portion 13.

In addition, a fourth valve 54d may be arranged on the recirculation portion 13 of the fluid circuit upstream the connection point between the first supply line 24a and the recirculation portion 13. Thus the connection point between the first supply line 24a and the recirculation portion 13 may be fluidly interposed between the first valve 54a and the fourth valve 54d. The fourth valve 54d may be fluidly interposed between this connection point and the second pump 70b. Thus, the second flow meter 82 may be interposed between the fourth valve 54d and the second pump 70b.

In addition to the first valve 54a, or alternatively to the first valve 54a, the at least one supplying valve may comprise a further valve 54a1 arranged on the first supply line 24a and interposed between the recirculation portion 13 and the first bag 38a. The further valve 54a1 is movable between an open position wherein fluid flow is allowed from the first bag 38a to at least a tract of the recirculation portion 13, and a close portion wherein fluid flow is prevented from the first bag 38a to the recirculation portion 13.

The fluid circuit 10 may also comprise a fifth valve 54e arranged downstream the air trap 60, and downstream the heater 56. The fifth valve 54e may be arranged between an outlet of the air trap 60 and an inlet of the first pump 70a, to selectively allow and prevent dialysis fluid to be delivered to the first pump 70a. When the fifth valve 54e is in a close position, fluid flow to the first pump 70a is prevented. On the contrary, when the fifth valve 54e is in open position, fluid flow to the first pump 70a is allowed. Notably, the first flow meter 81 may be arranged between the fifth valve 54e and the first pump 70a.

The fluid circuit 10 may also comprise a sixth valve 54f arranged on the delivery line 11 downstream the first pump 70a. The sixth valve 54f may be interposed between an outlet of the first pump 70a and the second end 28b of the patient line 28. Thus the sixth valve 54f may be configured to selectively allow and prevent fluid flow from the first pump 70a to the patient line 28, in particular to the filling line of the patient line 28.

The fluid circuit 10 may also comprise an auxiliary valve, not shown in the attached figures, arranged on the withdrawal line 12 upstream of the second pump 70b. The auxiliary valve may be interposed between an inlet of the second pump 70b and the second end 28b of the patient line 28. Thus the auxiliary valve may be configured to selectively allow and prevent fluid flow from the patient line 28 to the second pump 70b, in particular from the sucking line of the patient line 28 to the second pump 70b.

The air trap 60 may comprise a vent line 52v connected to a top portion of the air trap 60 and configured to extract air or gasses out of the air trap 60. The vent line 52v may be connected to the discharging line 14, so that air or gasses may be discharged out of the fluid circuit. In one embodiment, the vent line 52v may employ one or more cross, marked via an X, with the loop circuit, in particular with the recirculation portion 13 of the fluid circuit 10. When the vent line 52v crosses the loop circuit, further valves may be provided: for example a seventh valve 54g, an eighth valve 54h, and a ninth valve 54h2 may be provided in the fluid circuit, wherein the seventh valve 54g is interposed between the air trap 60 and a first cross X with loop circuit, the eighth valve 54h is interposed between the first cross and a second cross of the vent line with the loop circuit, and the ninth valve 54h2 may be arranged between the second cross and the outlet of the vent line or between the second cross and discharging line 14. Alternatively, the vent line 52v line may extend between the air trap 60 and an outlet, i.e. at the discharging line 14, without crossing the loop circuit. Alternatively, the vent line 52v line may extend between the air trap 60 and a free end configured to exit the gases in the atmosphere.

The fluid circuit 10 further comprises a the discharging valve 54i arranged on the discharging line 14 and movable between an open position, wherein fluid passage is allowed through the discharging line 14, and a close position, wherein fluid passage is prevented through the discharging line 14. The control unit 100 may be configured to command the discharging valve 54i selectively in the close position and in the open position.

The apparatus 20 may comprise a leak detection pan 83, located at the bottom of housing 22, and a corresponding leak detection sensor 85 outputting to control unit 100. Leak detection pan 83 may be made of any of the materials and is angled or funneled to have an angle or funnel shape, which collects any type of fluid (fresh or used PD fluid, disinfection fluid, flush flow fluid, RO or distilled water) that falls from the reusable tubing of apparatus 20 due to a faulty connection, ruptured material, or other reason. Leak detection sensor 85 in one embodiment does not contact the leaked fluid directly and may be any type of sensor for level sensors, e.g., ultrasonic, inductive, capacitive and/or optical. Leak detection sensor 85 may alternatively directly contact the leaked material, e.g., via an electrical contact closure sensor.

Combinations of different types of sensors 85 and multiple sensors 85 may be provided as needed. Upon receiving a fluid leak signal from leak detection sensor 85, control unit 100 alarms.

A filter set 40 may be provided on the patient line 28 to provide a final stage of PD fluid filtration prior to delivery to the patient.

As shown in the attached figures, a tract of the recirculation portion 13 interposed between the first valve 54a and the heater 56 is referred to as 52a1. Furthermore, a tract of the recirculation portion 13 interposed between the heater 56 and the air trap 60 is referred to as 52b.

A tract of the recirculation portion 13 interposed between the air trap 60 and the first pump 70a is referred to as 52c. Furthermore, a tract of the vent line 52v interposed between the valve 54h and the valve 54h2 is referred to as 52g. Furthermore, a tract of the vent line 52v interposed between the valve 54h2 and the discharging line 14 is referred to as 52h2. A tract of the preparation assembly 90 interposed between the second valve 54b and the main valve 154 is referred to as 52a2. A tract of the preparation assembly 90 interposed between the third valve 54c and the main valve 154 is referred to as 52a3.

FIG. 5 shows a further embodiment of the PD fluid circuit 10 illustrated in FIGS. 2 to 4.

System 10a includes many of the same components as system 10, which are generally numbered the same and include all structure, functionality, and alternatives discussed above for the previous system. For example, system 10a includes cycler 20 and control unit 100 having one or more processor 102, one or more memory 104, video controller 106 and user interface 108. System 10a includes inline dialysis fluid heater 56, reusable lines or tubes 52a and 52b, air trap 60 operating with respective upper and lower level sensors 62a and 62b, air trap valve 54d, vent valve 54e located along vent line 52e, reusable line or tubing 52c, dialysis fluid pumps 70a and 70b, temperature sensors 58a and 58b, reusable line or tubing 52d, pressure sensors 78a, 78b1, 78b2 and 78c, reusable patient tubing or lines 52f and 52g, hose reel 110, dual lumen reusable patient line 28, reusable drain tubing or line 52i extending to drain line connector 34 and having a drain line valve 54i, and reusable recirculation disinfection tubing or lines 52r1 and 52r2 operating with respective disinfection valves 54r1 and 54r2. A third recirculation or disinfection tubing or line 52r3 extends between disinfection connectors 30a and 30b for use during disinfection. A fourth recirculation or disinfection tubing or line 52r4 extends between disinfection connectors 30c and 30e for use during disinfection.

One primary difference with system 10 is that system 10a further includes a fourth PD fluid container or bag 38e that connects to a distal end 24d of reusable PD fluid lines 24e. Fourth PD fluid container or bag 38e may hold the same or different type of PD fluid as PD fluid containers or bags 38a to 38c. Reusable PD fluid lines 24a to 24c and 24e extend in one embodiment from apertures 26 defined or provided by housing 22 of cycler 20 (see FIG. 1).

System 10a accordingly includes four disinfection connectors 30a to 30c and 30e for connecting to distal ends 24d of reusable PD fluid lines 24a to 24c and 24e, respectively, during disinfection.

Three-way valve 154a in the illustrated embodiment allows for control unit 100 to select between (i) 2.27% glucose dialysis fluid from container or bag 38b or 38e and (ii) icodextrin from container or bag 38c. In the illustrated embodiment, icodextrin from container or bag 38c is connected to the normally closed port of three-way valve 154a.

The fluid circuit of FIG. 5 includes a source of acid, such as a citric acid container or bag 66.

Citric acid container or bag 66 is in selective fluid communication with a second three-way valve 154b via a citric acid valve 54m located along a citric acid line 52m. Citric acid line 52m is connected in one embodiment to the normally closed port of second three-way valve 154b, to provide redundant valves between citric acid container or bag 66 and the PD fluid circuit during treatment.

As already mentioned before, the apparatus 20 comprises the control unit 100: the control unit 100 may be contained in the internal volume of the housing 22. The control unit 100 may have one or more processors 102 and one or more memories 104 that may receive, store and process signals or outputs from the pressure sensors 78a and 78b, temperature sensors 58a and 58b, the conductivity sensor 74, first flow meter 81, second flow meter 82.

The control unit is also operatively connected to the first pump 70a and to the second pump 70b: the control unit may be configured to command activation and stop of the first pump 70a and of the second pump 70b, and to control them in speed and/or based on a desired flow rate.

Notably, the control unit 100 is configured to control the first pump 70a and the second pump 70b independently, so that the first pump may be commanded at a first flow rate or at a first speed, and the second pump may be commanded at a second flow rate or at a second speed different from the first flow rate/speed. The first flow rate and the second flow rate may be varied by the control unit 100.

The control unit 100 is also operatively connected to the valves from 54a to 54h2, the auxiliary valve, the main valve 154, and the discharging valve 54i, as previously described, of the fluid circuit. The control unit 100 may be configured to open and close the valves, i.e. according to a predefined procedure, defining different configurations of the fluid circuit. For example the control unit 100 may be configured to command the valves of the fluid circuit to deliver dialysis fluid to the patient's abdomen, or to suck spent dialysis fluid from the patient's abdomen after a dwell time.

The control unit 100 is also operatively connected to the conductivity sensor 74 to monitor the fluid conductivity. The control unit 100 may also control the supply valves between the fluid preparation assembly 90 and the loop circuit to vary a conductivity of the dialysis fluid.

The apparatus 20 may also comprise a video controller 106, operatively connected to the control unit 100 that interfaces with a user interface 108, which may include a display screen operating with a touchscreen and/or one or more electromechanical button, such as a membrane switch. User interface 108 may also include one or more speaker for outputting alarms, alerts and/or voice guidance commands. User interface 108 may be provided with apparatus 20 as illustrated in FIG. 1 and/or be a remote user interface operating with control unit 100. Control unit 100 may also include a transceiver (not illustrated) and a wired or wireless connection to a network, e.g., the internet, for sending treatment data to and receiving prescription instructions from a doctor's or clinician's server interfacing with a doctor's or clinician's computer.

Notably in the FIGS. 2-4, darkened valves are open at least at some point within the sequence, while the empty valves are in the close position. The arrows show one embodiment for the direction of fresh or used dialysis fluid flow.

Peritoneal Dialysis Procedure

The following invention is directed to a peritoneal dialysis procedure 200 for performing a peritoneal dialysis treatment to a patient. The peritoneal dialysis procedure 200 is performed by the control unit 100: in particular all the steps described here after or in the claims/aspects are performed by the control unit 100.

The peritoneal dialysis procedure 200 comprises a step of commanding activation 201 of the first pump 70a at a first flow rate, and activation 202 of the second pump 70b at a second flow rate different from the first flow rate. Notably, during the peritoneal dialysis procedure and thus during the peritoneal treatment, the first pump 70a and the second pump 70b are active simultaneously to deliver the first flow rate and the second flow rate. In particular, during the peritoneal treatment, both the first pump 70a and the second pump 70b rotating elements rotate.

The first flow rate may be in a range between 100 ml/min and 1500 ml/min. Analogously, the second flow rate may be in a range between 100 ml/min and 1500 ml/min. Notably, both ranges are different and may even not include some of the desired filling flow rates to or desired emptying flow rates from the patient required at the patient line 28, namely a low flow rate in the range of 15 to 100 ml/min. The first flow rate and the second flow rate may correspond to a condition wherein the first pump 70a and the second pump 70b work around an optimal condition, for example around an optimal condition in terms of efficiency or optimal condition wherein the current flow rate provided by the pump substantially correspond to the flow rate commanded (e.g., 500/600 ml/min).

The peritoneal dialysis procedure 200 may comprise a step of determining or receiving an optimal first flow rate and/or an optimal second flow rate. The optimal first flow rate and/or the optimal second flow rate represent in particular an optimal operating range for the first pump 70a and for the second pump 70b.

Based in the architecture of the fluid circuit 10 described above, a difference between the first flow rate and the second flow rate defines an exchange parameter value representing the exchange flow rate of dialysis fluid with the patient. In other terms, the difference between the first flow rate and the second flow rate determines either a filling procedure 203, wherein the patient abdomen is filled with dialysis fluid through the patient line 28, or a drainage procedure 204 wherein spent dialysis fluid is sucked from the patient abdomen through the patient line 28.

During the filling procedure, shown in FIGS. 2-3 and 5, the first flow rate is greater than the second flow rate. On the contrary, during the drainage procedure, shown in the FIG. 4, the first flow rate is smaller than the second flow rate. Thus, it should be noted that the current flow rate for filling the patient's abdomen is not determined by the rotational speed of a single pump, while it is determined by the differential in flow rate/speed between the first and the second pumps 70a, 70b. For example, when the first pump 70a is set at 220 ml/min and the second pump is set at 200 ml/min, the patient's abdomen is filled at a flow rate of 20 ml/min. On the contrary, when the first pump 70a is set at 200 ml/min and the second pump is set at 220 ml/min, the patient's abdomen is emptied at a flow rate of 20 ml/min. The patient filling may be achieved using flow rates in the patient line that vary during the filling step. Higher flow rates may be used at the beginning of the filling phase (e.g., 350 ml/min) followed by lower flow rates (e.g., 20 ml/min) after e.g., 5 minutes or 2-L infusion. Lower infusion rates may be lower than 50 ml/min. In low fill mode, flow rates lower than 15 mil/min may be used.

As already mentioned, each dwell is followed by a complete drain, after which the peritoneal cavity is filled again with fresh dialysate. The outflow of drained fluid may be biphasic, having a "fast phase" with flow rates of about 350 ml/min, and a "slow phase" with significantly lower flows, being only 30 to 40 ml/min (or less). The separation between the fast and slow outflow phase is called the transition or break point, which usually occurs after 5 minutes after a 2-L dwell.

Then the peritoneal dialysis procedure 200 may comprise a step of determining a working time, for example between 30 seconds and 20 minute, to fill the patient's abdomen with a predefined amount of dialysis fluid. Analogously, the peritoneal dialysis procedure 200 may comprise a step of determining a working time, for example between 30 seconds and 20 minute, to remove from the patient's abdomen a predefined amount of spent dialysis fluid.

The peritoneal dialysis procedure may further comprise a step of calculating the exchange parameter value based on a difference between the first flow rate and the second flow rate. The exchange parameter value may be calculated based, in addition, on an operating time of the peritoneal dialysis procedure, in particular an operating time of the filling procedure and of the drainage procedure.

The peritoneal dialysis procedure may further or alternatively comprise a step of receiving as input a desired value of the exchange parameter representing the exchange flow rate of dialysis fluid with the patient, and then setting a difference between the first flow rate and the second flow rate based on the desired exchange parameter value received as input, in order to obtain the desired exchange parameter value.

In the embodiment comprising the first flow meter 81 and the second flow meter 82, the first flow rate delivered by the first pump goes through the first flow meter 81, while the second flow rate delivered by the second pump 70b goes through the second flow meter 82.

During the peritoneal dialysis procedure, the first flow meter 81 and the second flow meter 82 may be configured to measure the current flow rate respectively in the delivery line 11 and in the withdrawal line 12. Thus, the peritoneal dialysis procedure may comprise calculating a current first flow rate measured by the first flow meter, and/or calculating a current second flow rate measured by the second flow meter.

Then the peritoneal dialysis procedure may comprise calculating the exchange parameter value, namely a current exchange parameter value, based on a difference between the current first flow rate and the current second flow rate measured by the first and the second flow meters 81, 82. In other terms, the first and the second flow meters 81, 82 allows to check the current flow rate determined by the first pump 70a and by the second pump 70b. If the current first flow rate differs from a desired first flow rate over a predefined threshold, the control unit may be configured to command an adjustment to the first pump 70a, until the difference between the current first flow rate and the desired first flow rate is lower than the predefined threshold.

Analogously, if the current second flow rate differs from a desired second flow rate over a predefined threshold, the control unit 100 may be configured to command an adjustment to the second pump 70b, until the difference between the current second flow rate and the desired second flow rate is lower than the predefined threshold.

Furthermore, the peritoneal dialysis procedure 200 may comprise adjusting the first pump 70a and/or the second pump 70b based on the actual exchange parameter value, namely the exchange parameter value calculated as the difference between the current first flow rate and the current second flow rate measured by the first and the second flow meters 81, 82. For example, if the exchange parameter value is too low or too high, the peritoneal dialysis procedure may adjust the first pump and/or the second pump, in order to vary the difference in flow rate between the first pump and the second pump. For example, if the actual exchange parameter value for filling the patient with dialysis fluid is lower than the desired exchange parameter value, the control unit 100 may command the first pump 70a to increase the first flow rate or may command the second pump 70b to reduce the second flow rate or may command both increase of the first flow rate and decrease of the second flow rate.

Furthermore, the filling procedure 203 may comprise the steps of calculating a filling fluid amount of dialysis fluid currently present in the patient abdomen based on the exchange parameter value, comparing the filling fluid amount with a maximum fluid amount threshold, and commanding a stop of the first pump and of the second pump when the filling fluid amount overcomes the maximum fluid amount threshold. The maximum fluid amount threshold may represent the maximum amount of dialysis fluid that the patient's abdomen is able to receive during the filling procedure.

Analogously, the drainage procedure 204 may comprise the steps of calculating a drainage fluid amount of dialysis fluid currently present in the patient abdomen based on the exchange parameter value, comparing the drainage fluid amount with a minimum fluid amount threshold, and then commanding a stop of the first pump and of the second pump when the drainage fluid amount becomes lower than the minimum fluid amount threshold.

Notably, the peritoneal dialysis procedure may comprise interposing a dwell time between an end of the filling procedure and a subsequent start of the drainage procedure: the dwell time may be comprised between 1 min and 360 min.

Analogously, the peritoneal dialysis procedure may comprise interposing a waiting time between an end of the drainage procedure and a subsequent start of the filling procedure: the waiting time may be comprised between 1 min and 20 min.

The peritoneal dialysis procedure may comprise the step of performing the filling procedure and the drainage procedure in subsequent cycles.

During the filling procedure 203, the peritoneal dialysis procedure may comprise a step, performed by the control unit 100, to command one or more of the supplying valves 54a, 54b, 54c, 154 to allow dialysis fluid to enter the recirculation portion of the fluid circuit. For example, the filling procedure 203 may comprise moving the first valve 54a in the open position to put the container or bag 38a in fluid communication with the loop circuit, in particular with the recirculation portion 13 of the fluid circuit. Alternatively, the filling procedure may comprise moving the second valve 54b in the open position to put the container or bag 38b in fluid communication with the loop circuit, in particular with the recirculation portion 13 of the fluid circuit. Alternatively, the filling procedure may comprise moving the third valve 54c in the open position to put the container or bag 38c in fluid communication with the loop circuit, in particular with the recirculation portion 13 of the fluid circuit. In an embodiment, the filling procedure may comprise moving the first, second and third valves 54a, 54b, 54c in the open position to put the containers or bags 38a, 38b, 38c in fluid communication with the loop circuit, in particular with the recirculation portion 13 of the fluid circuit. In another embodiment, the filling procedure may comprise moving the second and third valves 54b, 54c in the open position to put the containers or bags 38b, 38c in fluid communication with the loop circuit, in particular with the recirculation portion 13 of the fluid circuit.

In another embodiment, the filling procedure may comprise moving the main valve 154 in the open position to put the containers or bags 38b, 38c, and optionally the first container, in fluid communication with the loop circuit, in particular with the recirculation portion 13 of the fluid circuit. The step of moving one or more of the supplying valves 54a, 54b, 54c, 154 in the open position during the filling procedure 203, causes the dialysis fluid to be sucked into the loop circuit, due to the difference in speed/flowrate between the first pump 70a and the second pump 70b. Notably, during the filling procedure, the discharging valve 54i is maintained in the close position: in particular the control unit 100 commands the discharging valve 54i in the close position. During the drainage procedure 204, the peritoneal dialysis procedure may comprise a step, performed by the control unit, to command the discharging valve 54*i* in the open position. During the drainage procedure 204, the first pump 70*a* delivers a first flow rate lower than the second flow rate of the second pump 70*b*: this difference causes an fluid over pressure downstream the second pump 70*b* and upstream the first pump, namely in the recirculation portion 13. The over pressure in the recirculation portion causes the dialysis fluid to be discharged through the discharging line 14, as the discharging valve 54*i* is in the open position.

Analogously, the difference between the first flow rate and the second flow rate during the drainage procedure 204 determines a sucking step of dialysis fluid from the patient's abdomen through the patient line 28, in particular through the sucking line of the patient line 28. In this way, the spent dialysis fluid is sucked from the patient and discharged through the discharging line. During the drainage procedure, the peritoneal dialysis procedure comprises a step of fluidly disconnecting the loop circuit from the preparation assembly 90: in particular the peritoneal dialysis procedure comprises moving one or more of the supply valves 54*a*, 54*b*, 54*c*, 154 in the close position to fluidly separate the loop circuit from the preparation assembly 90. Thus, during the drainage procedure, the dialysis fluid flows in loop in the loop circuit while being discharged through the discharging line 14.

Notably, both during the filling procedure and during the drainage procedure, the first pump 70*a* and the second pump 70*b* work simultaneously at different flow rates.

The invention claimed is:

1. A peritoneal dialysis ("PD") fluid circuit comprising:
a patient line extending between a first end configured to connect to a patient's abdomen and a second end;
a fluid recirculation loop comprising:
   a delivery line connected to the second end of the patient line to supply fresh dialysis fluid towards the patient line; and
   a withdrawal line connected to the second end of the patient line to withdraw spent dialysis fluid from the patient line;
a first pump arranged on the delivery line to supply the fresh dialysis fluid towards the patient line;
a second pump arranged on the withdrawal line to withdraw the spent dialysis fluid from the patient line,
wherein the fluid recirculation loop further comprises a recirculation portion extending from an outlet of the second pump up to an inlet of the first pump according to a fluid direction defined by the first pump and the second pump, the recirculation portion not including the second end of the patient line,
wherein the fluid direction is defined from the first pump towards the patient line, and from the patient line to the second pump, and from the second pump towards the recirculation portion, and
wherein the delivery line, the withdrawal line and the recirculation portion are fluidly connected to each other in series defining the fluid recirculation loop; and
a control unit operatively connected to the first pump and to the second pump, the control unit being configured to perform a peritoneal dialysis procedure comprising the step of:
   commanding activation of the first pump at a first flow rate, and commanding activation of the second pump at a second flow rate different from the first flow rate,
   wherein the first pump and the second pump are active simultaneously to provide the first flow rate and the second flow rate, wherein the control unit is further configured to cause dialysis fluid to circulate in the fluid recirculation loop through the first pump and the second pump during the peritoneal dialysis procedure.

2. The peritoneal dialysis ("PD") fluid circuit of claim 1, wherein a difference between the first flow rate and the second flow rate defines an exchange parameter value representing an exchange flow rate of the dialysis fluid with the patient in the patient line,
   wherein, during the peritoneal dialysis procedure, the control unit is further configured to either:
   calculate the exchange parameter value based on the difference between the first flow rate and the second flow rate; or
   receive, as an input, a desired exchange parameter value representing a desired exchange flow rate of the dialysis fluid with the patient in the patient line; and
   set a difference between the first flow rate and the second flow rate based on the desired exchange parameter value to obtain the desired exchange flow rate of the dialysis fluid in the patient line.

3. The peritoneal dialysis ("PD") fluid circuit of claim 1, wherein, during the peritoneal dialysis procedure, the control unit is further configured to:
   receive an optimal first flow rate comprised between 100 ml/min and 1500 ml/min and an optimal second flow rate comprised between 100 ml/min and 1500 ml/min, the first flow rate and the second flow rate representing an optimal operating condition for the first pump and for the second pump;
   set the first flow rate of the first pump within a first range of 30% of the optimal first flow rate; and
   set the second flow rate of the second pump within a second range of +30% of the optimal second flow rate;
   cause the first flow rate to be in a range between 100 ml/min and 1500 ml/min; and
   cause the second flow rate to be in a range between 100 ml/min and 1500 ml/min.

4. The peritoneal dialysis ("PD") fluid circuit of claim 1, wherein, during the peritoneal dialysis procedure, the control unit is further configured to execute
   a filling procedure to fill the patient's abdomen with the dialysis fluid through the patient line, during the filling procedure the first flow rate being higher than the second flow rate, and
   a drainage procedure to remove the spent dialysis fluid from the patient's abdomen through the patient line, during the drainage procedure the first flow rate being lower than the second flow rate,
   the control unit being configured to alternate the filling procedure and the drainage procedure.

5. The peritoneal dialysis ("PD") fluid circuit of claim 4, wherein, during the peritoneal dialysis procedure, the control unit is further configured to interpose a dwell time between an end of the filling procedure and a subsequent start of the drainage procedure, the dwell time being comprised between 1 min and 360 min,
   and wherein, during the peritoneal dialysis procedure, the control unit is further configured to interpose a waiting time between an end of the drainage procedure and a subsequent start of the filling procedure, the waiting time being less than 20 min.

6. The peritoneal dialysis ("PD") fluid circuit of claim 1, wherein the first pump is a volumetric pump, the first pump being one of a reciprocating pump, a peristaltic pump, a membrane pump, a gear pump, and a piston pump,

wherein the second pump is a volumetric pump, the second pump being one of a reciprocating pump, a peristaltic pump, a membrane pump, a gear pump, and a piston pump, and wherein the first pump and the second pump are of the same type.

7. The peritoneal dialysis ("PD") fluid circuit of claim 1, further comprising a discharging line connected to the recirculation portion, wherein the discharging line extends from the recirculation portion to an outlet for draining the dialysis fluid, and wherein the control unit is further configured to drain the dialysis fluid through the discharging line during a drainage procedure.

8. The peritoneal dialysis ("PD") fluid circuit of claim 1, wherein the patient line comprises one of:

a dual lumen patient line combining in a single body a filling line connected to the delivery line to deliver the fresh dialysis fluid into the patient's abdomen, and a sucking line connected to the withdrawal line to remove the spent dialysis fluid from the patient's abdomen;

a filling line connected to the delivery line to deliver the fresh dialysis fluid into the patient's abdomen, and a sucking line connected to the withdrawal line to remove the spent dialysis fluid from the patient's abdomen, wherein the filling line is distinct from the sucking line; and a single lumen line for alternatively sending and withdrawing the dialysis fluid into and from the patient's abdomen.

9. The peritoneal dialysis ("PD") fluid circuit of claim 1, further comprising:

a dialysis fluid heater to heat the dialysis fluid, wherein the dialysis fluid heater is arranged in a recirculation portion of the fluid recirculation loop; and an air trap to remove air bubbles from the dialysis fluid, the air trap being arranged on the recirculation portion of the fluid recirculation loop.

10. The peritoneal dialysis ("PD") fluid circuit of claim 1, further comprising a preparation assembly to prepare the dialysis fluid according to a predefined recipe, the preparation assembly comprising one or more supply lines for connection to a respective fluid source containing the dialysis fluid or a solution for preparing the dialysis fluid, wherein the one or more supply lines are configured, during a filling procedure, to deliver fluid to the recirculation portion of the PD fluid circuit.

11. The peritoneal dialysis ("PD") fluid circuit of claim 10, wherein the one or more supply lines comprise a first supply line and a second supply line respectively connected to a first fluid source and a second fluid source, and wherein the preparation assembly is configured to deliver the solution of the first fluid source and the solution of the second fluid source to the fluid recirculation loop.

12. The peritoneal dialysis ("PD") fluid circuit of claim 10, further comprising a supplying valve fluidly interposed between the one or more supply lines and the recirculation portion of the PD fluid circuit, the supplying valve being fluidly interposed between the one or more supply lines and the fluid recirculation loop, and the supplying valve being movable between an open position, wherein fluid is allowed to move from the one or more supply lines to the fluid recirculation loop, and a close position wherein fluid passage is prevented between the one or more supply lines and the fluid recirculation loop.

13. The peritoneal dialysis ("PD") fluid circuit of claim 12, wherein:

during the filling procedure, the control unit is further configured to execute the peritoneal dialysis procedure comprising a step to control the supplying valve in the open position to allow fluid to move from the preparation assembly to the recirculation portion; and during a drainage procedure, the control unit is further configured to execute the peritoneal dialysis procedure comprising a step to control the supplying valve in the close position.

14. A peritoneal dialysis ("PD") fluid circuit comprising:

a patient line extending between a first end, configured to connect to a patient's abdomen, and a second end;

a fluid recirculation loop comprising:

a delivery line connected to the second end of the patient line and configured to supply fresh dialysis fluid towards the patient line;

a withdrawal line connected to the second end of the patient line and configured to withdraw spent dialysis fluid from the patient line; and a discharging line connected to a recirculation portion, wherein the discharging line extends from the recirculation portion to an outlet for draining dialysis fluid;

a first pump arranged on the delivery line and configured to supply the fresh dialysis fluid towards the patient line;

a second pump arranged on the withdrawal line and configured to withdraw the spent dialysis fluid from the patient line, wherein the fluid recirculation loop further comprises the recirculation portion extending from an outlet of the second pump up to an inlet of the first pump according to a fluid direction defined by the first pump and the second pump, the recirculation portion not including the second end of the patient line, wherein the fluid direction is defined from the first pump towards the patient line, and from the patient line to the second pump, and from the second pump towards the recirculation portion, wherein the delivery line, the withdrawal line and the recirculation portion are fluidly connected to each other in series defining the fluid recirculation loop; and a control unit operatively connected to the first pump and the second pump, the control unit being configured to perform a peritoneal dialysis procedure comprising the step of:

commanding activation of the first pump at a first flow rate, and commanding activation of the second pump at a second flow rate different from the first flow rate, and circulating the dialysis fluid into the fluid recirculation loop through the first pump and the second pump, wherein the first pump and the second pump are active simultaneously to provide the first flow rate and the second flow rate, wherein, during the peritoneal dialysis procedure, the control unit is further configured to:

receive an optimal first flow rate comprised between 100 ml/min and 1500 ml/min and an optimal second flow rate comprised between 100 ml/min and 1500 ml/min, the optimal first flow rate and the optimal second flow rate representing an optimal operating condition for the first pump and for the second pump;

set the first flow rate of the first pump within a first range of 30% of the optimal first flow rate; and set the second flow rate of the second pump within a second range of +30% of the optimal second flow rate;

command the first flow rate in a range between 100 ml/min and 1500 ml/min; and command the second flow rate in a range between 100 ml/min and 1500 ml/min.

15. The peritoneal dialysis ("PD") fluid circuit of claim 14, further comprising:

a first flow meter configured to measure a current first flow rate provided by the first pump, the first flow meter being arranged in series with the first pump so that a same fluid flow rate flows through the first pump and the first flow meter, wherein the first flow meter is arranged on the fluid recirculation loop upstream of the first pump; and a second flow meter configured to measure a current second flow rate provided by the second pump, the second flow meter being arranged in series with the second pump so that a same fluid flow rate flows through the second pump and the second flow meter, wherein the second flow meter is arranged on the fluid recirculation loop downstream from the second pump or on the withdrawal line downstream from the second end of the patient line.

16. The peritoneal dialysis ("PD") fluid circuit of claim 15, wherein, during the peritoneal dialysis procedure, the control unit is further configured to:

determine the current first flow rate measured by the first flow meter;

determine the current second flow rate measured by the second flow meter;

calculate a current exchange parameter value based on a difference between the current first flow rate and the current second flow rate, the current exchange parameter value representing a current exchange flow rate of the dialysis fluid with the patient;

comparing the current exchange parameter value with a desired exchange parameter value; and based on the comparison, when a difference between the current exchange parameter value and the desired exchange parameter value exceeds a predefined threshold, adjusting a difference in flow rate between the first pump and the second pump towards the desired exchange parameter value by changing the first flow rate of the first pump and/or the second flow rate of the second pump.

17. The peritoneal dialysis ("PD") fluid circuit of claim 15, further comprising a discharging valve movable between an open position, wherein fluid is allowed to be discharged through the discharging line, and a close position wherein fluid passage through the discharging line is prevented, and wherein:

during a drainage procedure, the control unit is further configured to execute the peritoneal dialysis procedure comprising a step to control the discharging valve in the open position; and during a filling procedure, the control unit is further configured to execute the peritoneal dialysis procedure comprising a step to control the discharging valve in the close position.

18. A peritoneal dialysis ("PD") fluid circuit comprising:

a patient line extending between a first end configured to connect to a patient's abdomen and a second end;

a fluid recirculation loop comprising:

a delivery line connected to the second end of the patient line to supply fresh dialysis fluid towards the patient line; and a withdrawal line connected to the second end of the patient line to withdraw spent dialysis fluid from the patient line;

a first pump arranged on the delivery line to supply the fresh dialysis fluid towards the patient line;

a second pump arranged on the withdrawal line to withdraw the spent dialysis fluid from the patient line;

a first flow meter configured to measure a current first flow rate provided by the first pump, the first flow meter being arranged in series with the first pump so that a same fluid flow rate flows through the first pump and the first flow meter, wherein the first flow meter is arranged on the fluid recirculation loop upstream of the first pump;

a second flow meter configured to measure a current second flow rate provided by the second pump, the second flow meter being arranged in series with the second pump so that a same fluid flow rate flows through the second pump and the second flow meter, wherein the second flow meter is arranged on the fluid recirculation loop downstream from the second pump or on the withdrawal line downstream from the second end of the patient line, wherein the fluid recirculation loop further comprises a recirculation portion extending from an outlet of the second pump up to an inlet of the first pump according to a fluid direction defined by the first pump and the second pump, the recirculation portion not including the second end of the patient line, wherein the fluid direction is defined from the first pump towards the patient line, and from the patient line to the second pump, and from the second pump towards the recirculation portion; and a control unit operatively connected to the first pump and to the second pump, the control unit being configured to perform a peritoneal dialysis procedure comprising the step of:

commanding activation of the first pump at a first flow rate, and commanding activation of the second pump at a second flow rate different from the first flow rate, and wherein the first pump and the second pump are active simultaneously to provide the first flow rate and the second flow rate, filling the patient's abdomen with dialysis fluid through the patient line, during a filling procedure, the first flow rate being higher than the second flow rate, and removing the spent dialysis fluid from the patient's abdomen through the patient line, during a drainage procedure, the first flow rate being lower than the second flow rate, the control unit being configured to alternate the filling procedure and the drainage procedure, wherein, during the peritoneal dialysis procedure, the control unit is further configured to:

determine the current first flow rate measured by the first flow meter;

determine the current second flow rate measured by the second flow meter;

calculate a current exchange parameter value based on a difference between the current first flow rate and the current second flow rate, the current exchange parameter value representing a current exchange flow rate of the dialysis fluid with the patient;

compare the current exchange parameter value with a
desired exchange parameter value; and
based on the comparison, if when a difference between the
current exchange parameter value and the desired
exchange parameter value exceeds a predefined thresh-
old, adjust a difference in flow rate between the first
pump and the second pump towards the desired
exchange parameter value by changing rhe first flow
rate of the first pump and/or the second flow rate of the
second pump.

19. The peritoneal dialysis ("PD") fluid circuit of claim
18, wherein the delivery line, the withdrawal line and the
recirculation portion are fluidly connected to each other in
series defining the fluid recirculation loop,
and wherein the control unit is further configured to
circulate the dialysis fluid into the fluid recirculation
loop through the first pump and the second pump
during the peritoneal dialysis procedure.

* * * * *

32